(12) United States Patent
Desinger

(10) Patent No.: US 6,723,094 B1
(45) Date of Patent: Apr. 20, 2004

(54) ELECTRODE ASSEMBLY FOR A SURGICAL INSTRUMENT PROVIDED FOR CARRYING OUT AN ELECTROTHERMAL COAGULATION OF TISSUE

(76) Inventor: Kai Desinger, Rubensstr. 108, Berlin (DE), 12157

( * ) Notice: Subject to any disclaimer, the term of this patent is extended or adjusted under 35 U.S.C. 154(b) by 0 days.

(21) Appl. No.: 09/868,303

(22) PCT Filed: Dec. 17, 1999

(86) PCT No.: PCT/EP99/10079

§ 371 (c)(1),
(2), (4) Date: Jul. 30, 2001

(87) PCT Pub. No.: WO00/36985

PCT Pub. Date: Jun. 29, 2000

(30) Foreign Application Priority Data

Dec. 18, 1998 (DE) .......................... 198 58 599

(51) Int. Cl.⁷ .............................. A61B 18/18
(52) U.S. Cl. ......................... 606/50; 606/41
(58) Field of Search ............... 606/41, 45, 46, 606/48–50

(56) References Cited

U.S. PATENT DOCUMENTS

| 4,043,342 A | * | 8/1977 | Morrison, Jr. ............... 606/48 |
|---|---|---|---|
| 4,832,048 A | | 5/1989 | Cohen |
| 5,009,656 A | * | 4/1991 | Reimels ..................... 606/48 |
| 5,123,903 A | | 6/1992 | Quaid et al. |
| 5,167,619 A | | 12/1992 | Wuchinich |
| 5,330,470 A | * | 7/1994 | Hagen ........................ 606/42 |
| 5,728,130 A | | 3/1998 | Ishikawa et al. |
| 5,833,689 A | * | 11/1998 | Long .......................... 606/48 |
| 6,004,319 A | * | 12/1999 | Goble et al. ................ 606/48 |

FOREIGN PATENT DOCUMENTS

| DE | 197 39 699 A1 | 3/1999 |
|---|---|---|
| WO | WO 81/03272 | 11/1981 |
| WO | WO 95/10320 | 4/1995 |
| WO | WO 95/17855 | 7/1995 |
| WO | WO 96/18349 | 6/1996 |
| WO | WO 96/34569 | 11/1996 |
| WO | WO 97/00647 | 1/1997 |
| WO | WO 97/17009 | 5/1997 |
| WO | WO 98/19613 | 5/1998 |
| WO | WO 99/11186 | 3/1999 |
| WO | WO 99/15120 | 4/1999 |

* cited by examiner

*Primary Examiner*—Michael Peffley
(74) *Attorney, Agent, or Firm*—Beck & Tysver, PLLC

(57) ABSTRACT

There is provided a surgical instrument for electrothermal coagulation of tissue, which includes a front cylinder at the distal end of the instrument having a distal tip, an elongate carrier, and two spaced cylindrical or strip-shaped electrodes at or on the carrier which are connectable to an HF-ac voltage source.

26 Claims, 16 Drawing Sheets

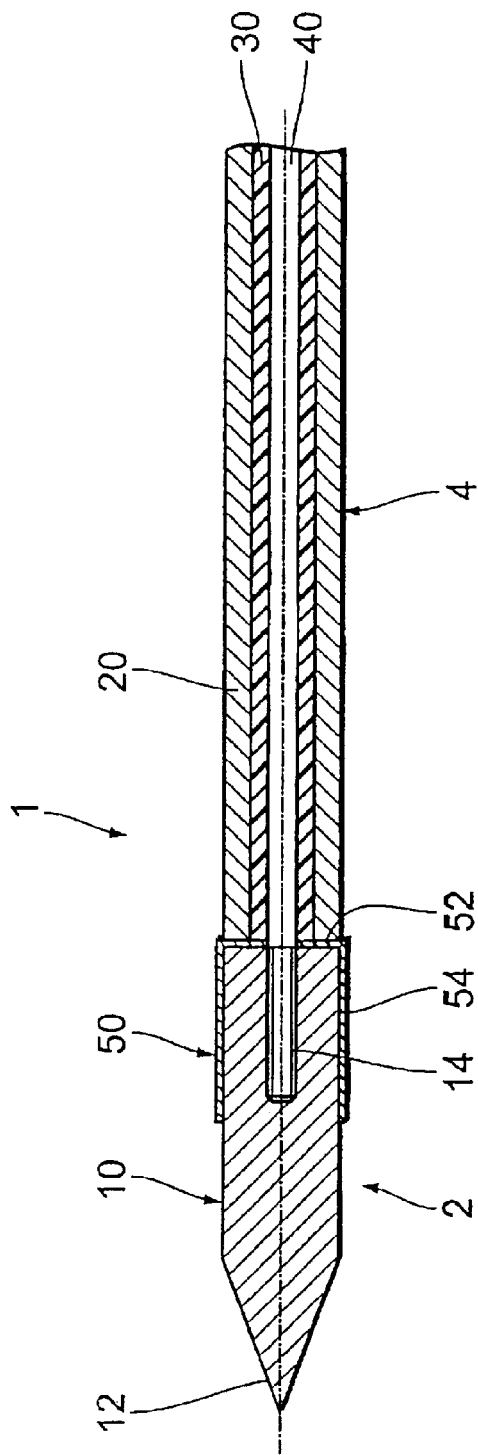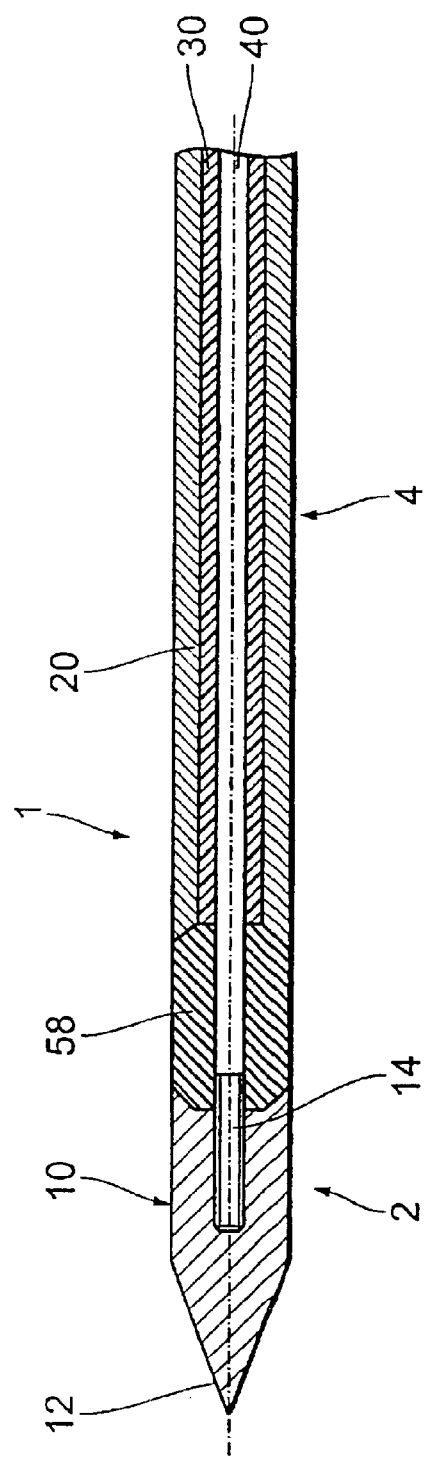

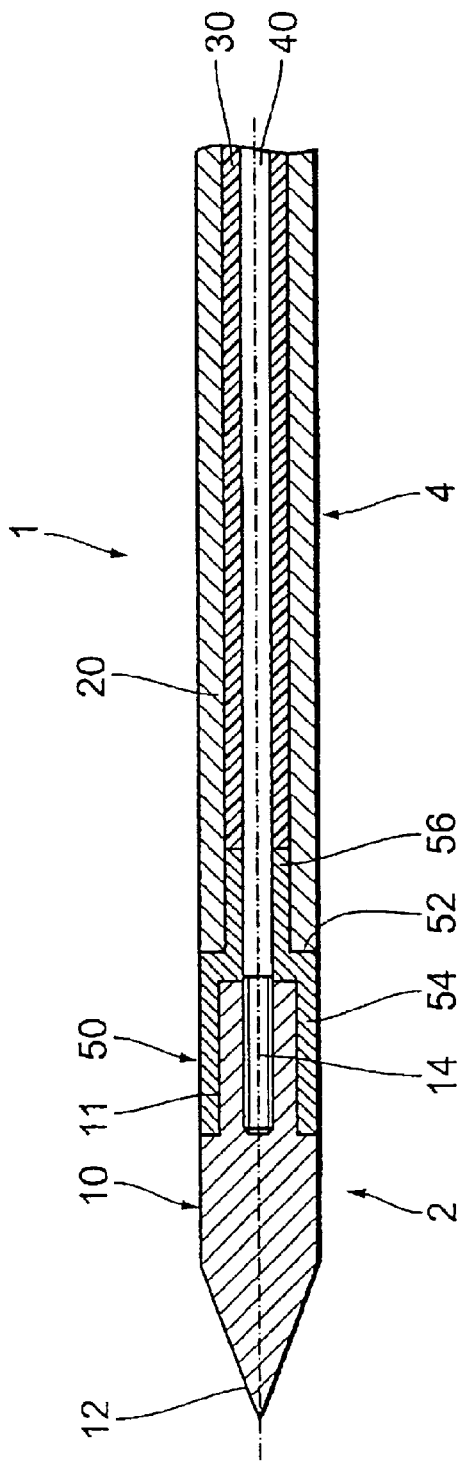
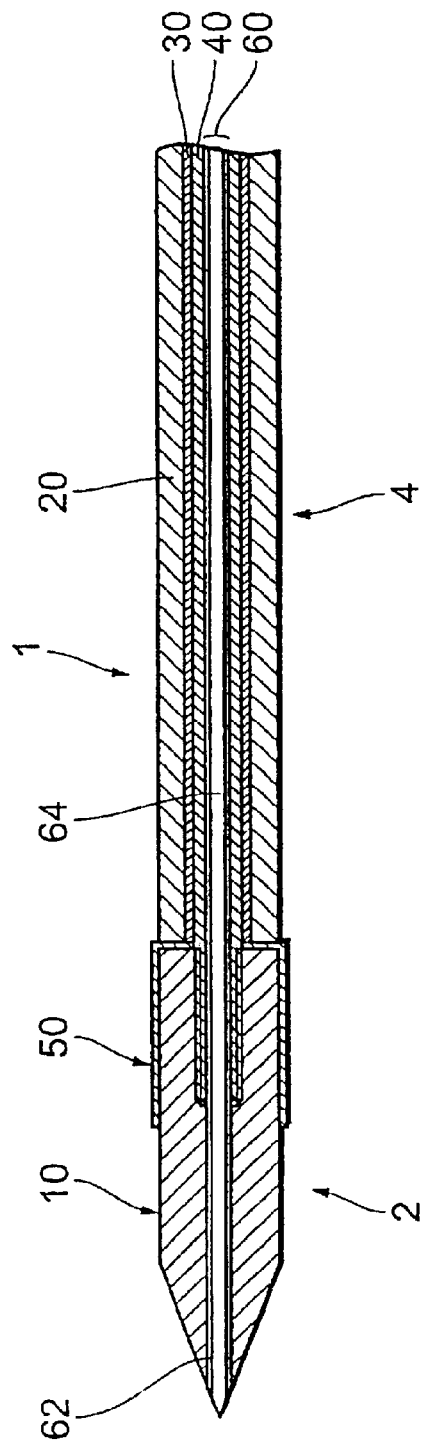

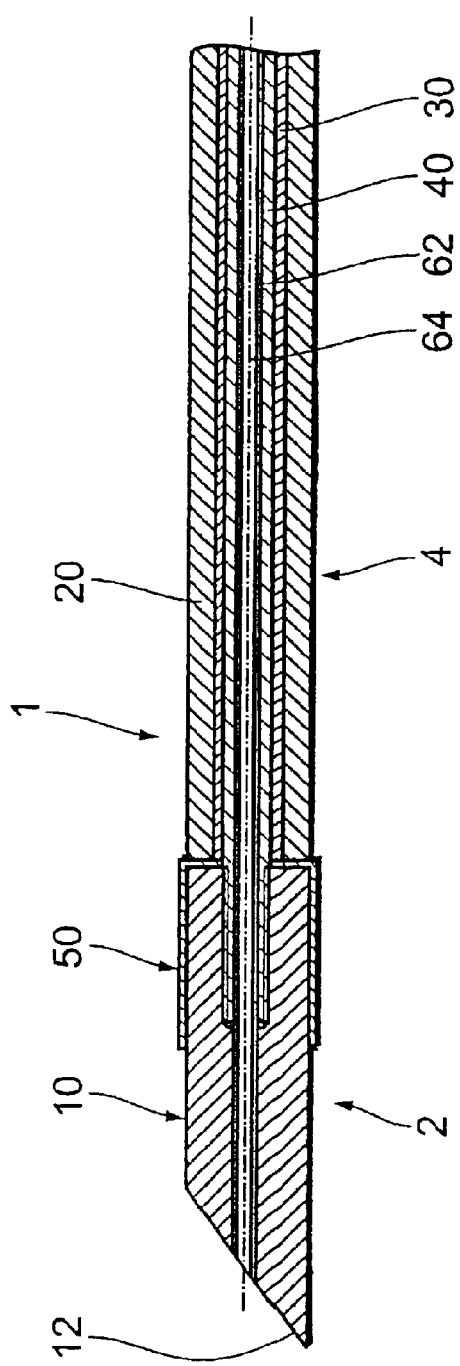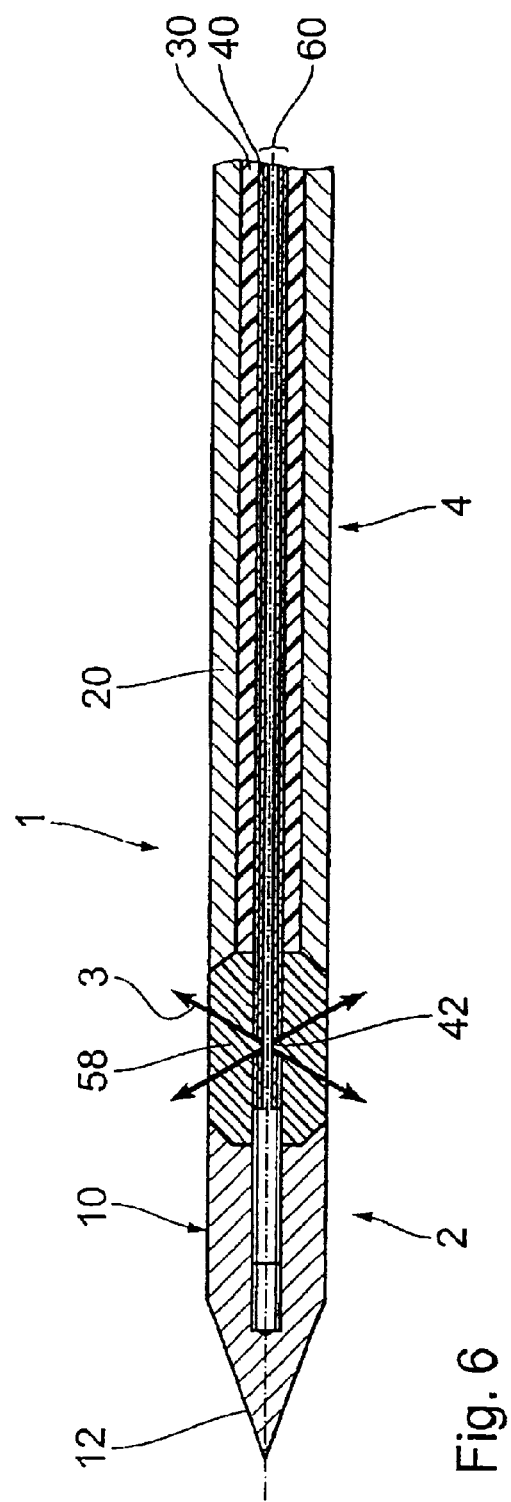
Fig. 5
Fig. 6

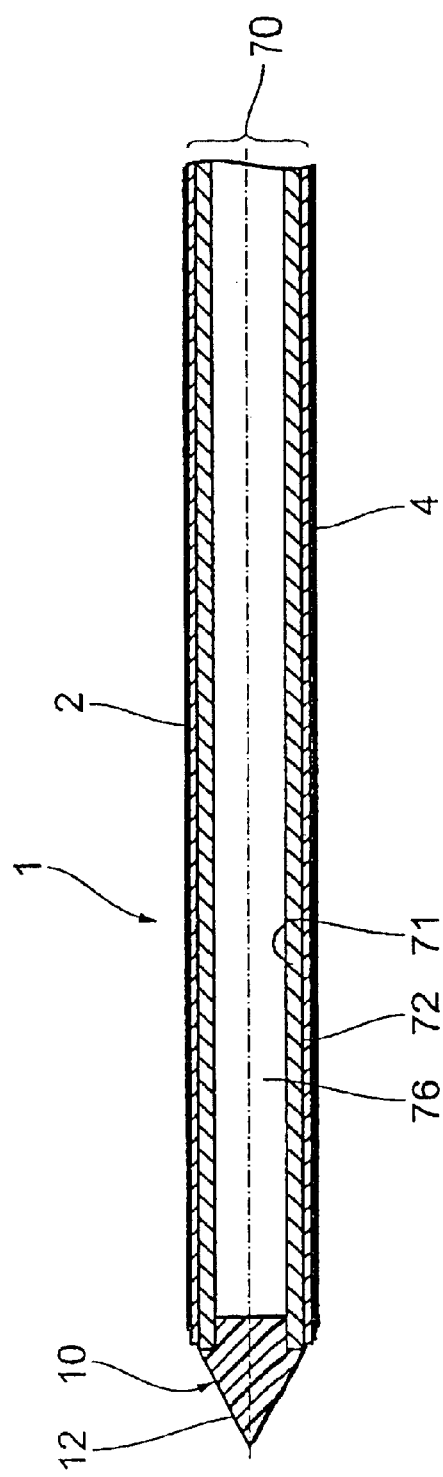
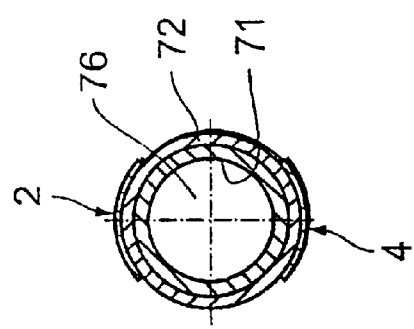
Fig. 7
Fig. 8

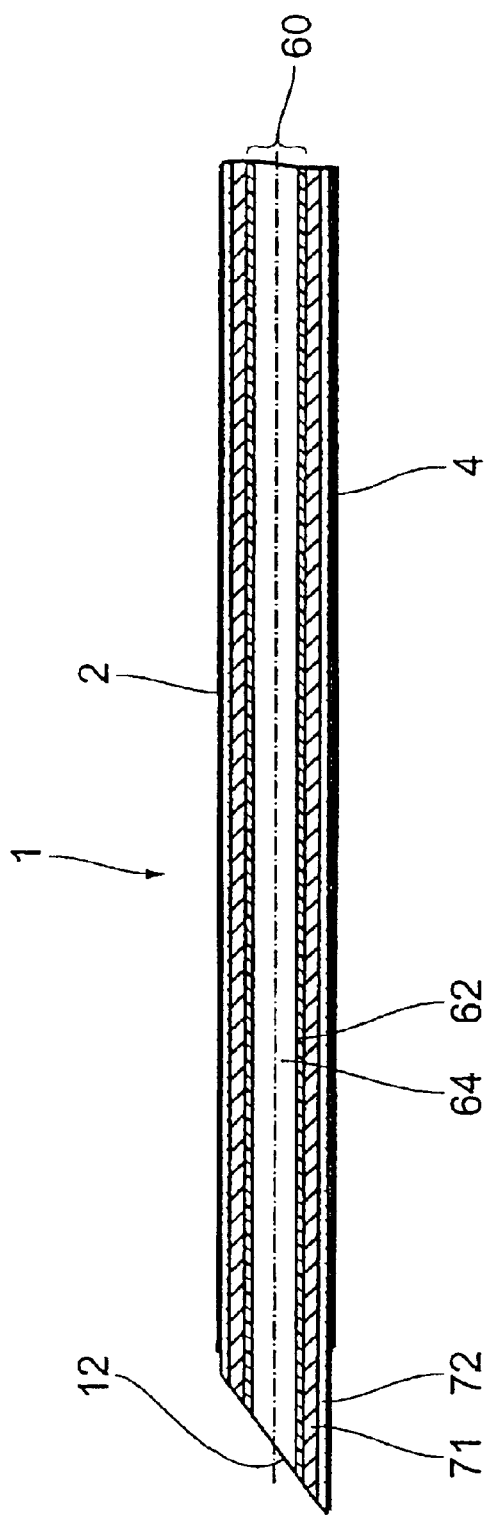
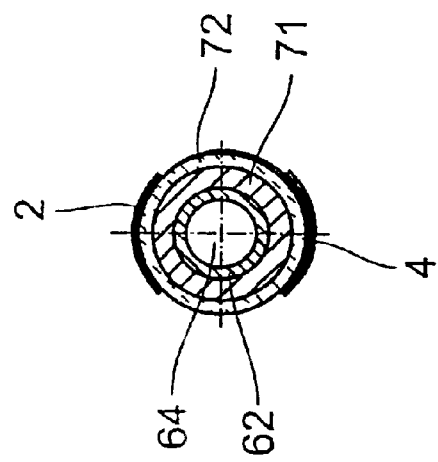
Fig. 9
Fig. 10

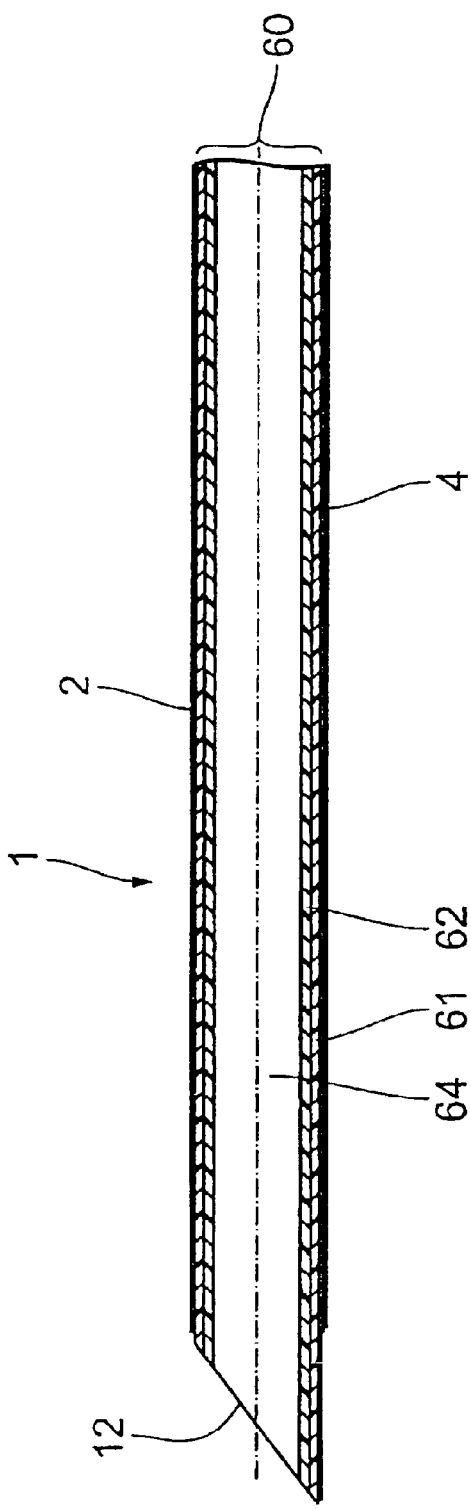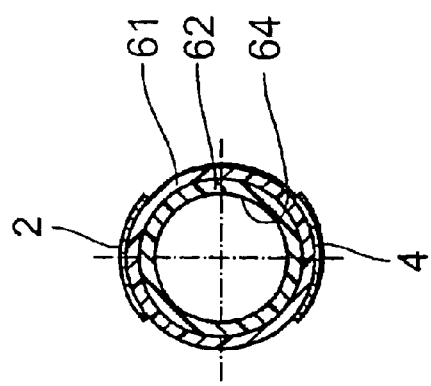
Fig. 11
Fig. 12

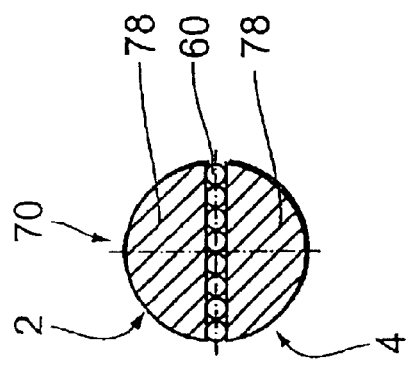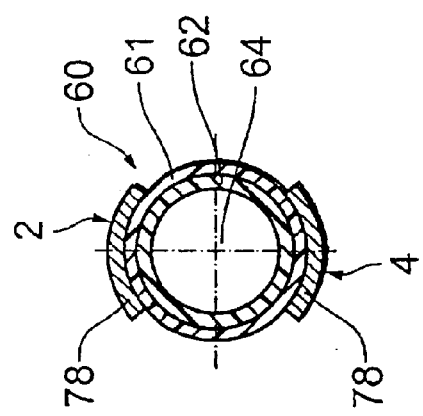

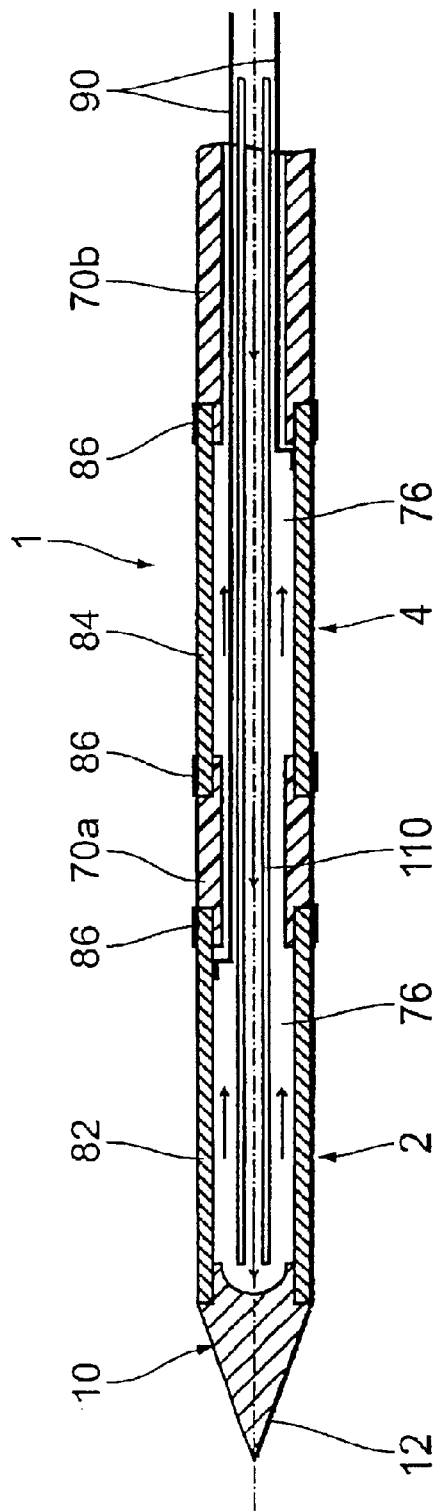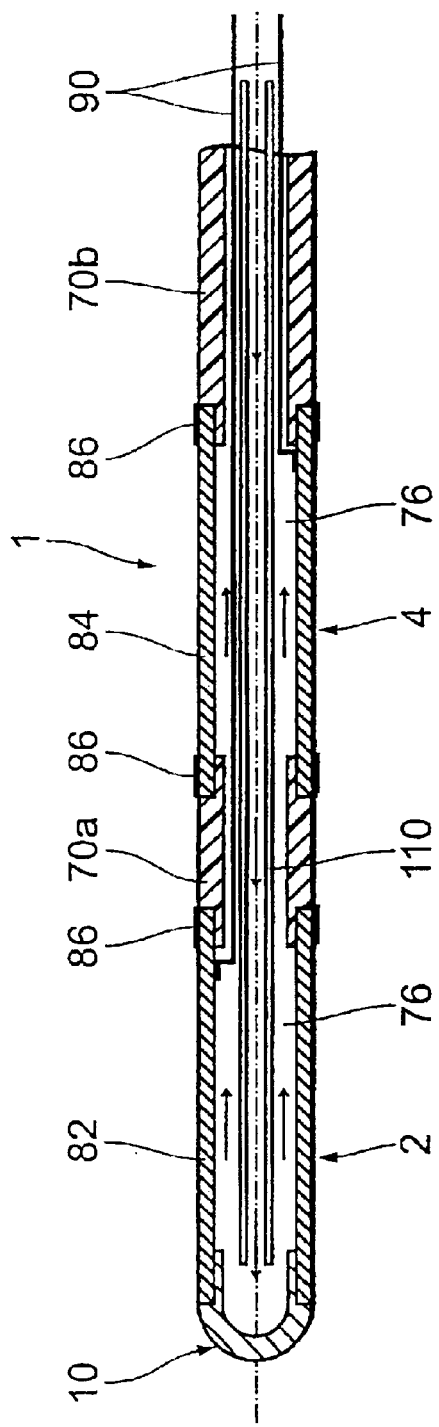
Fig. 18
Fig. 19

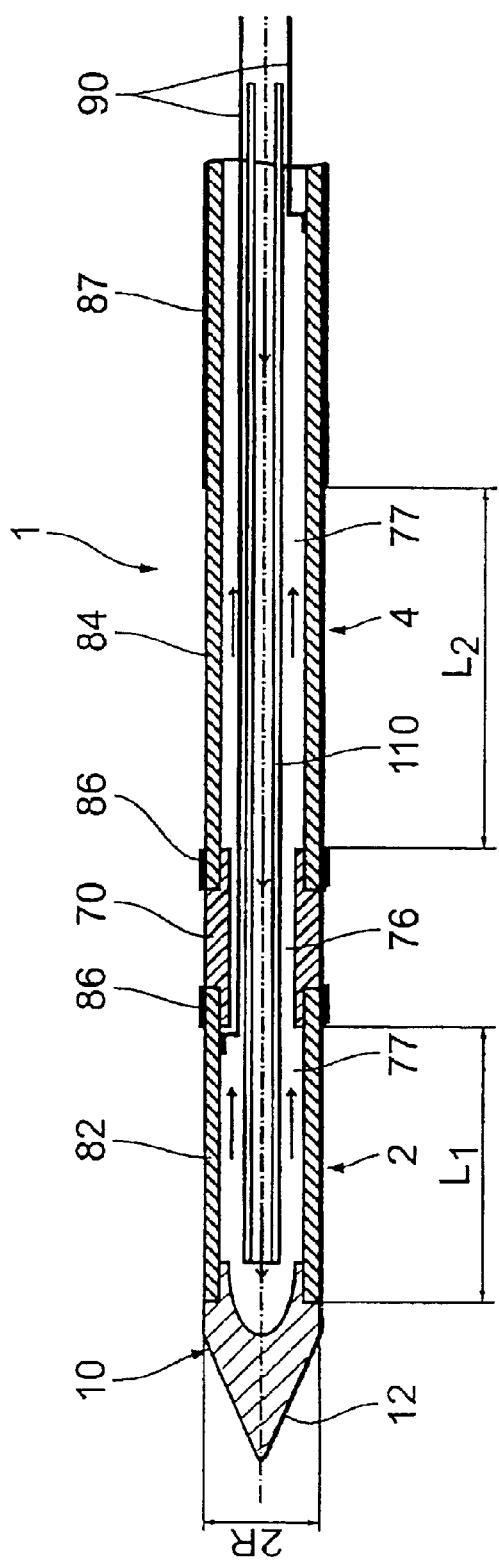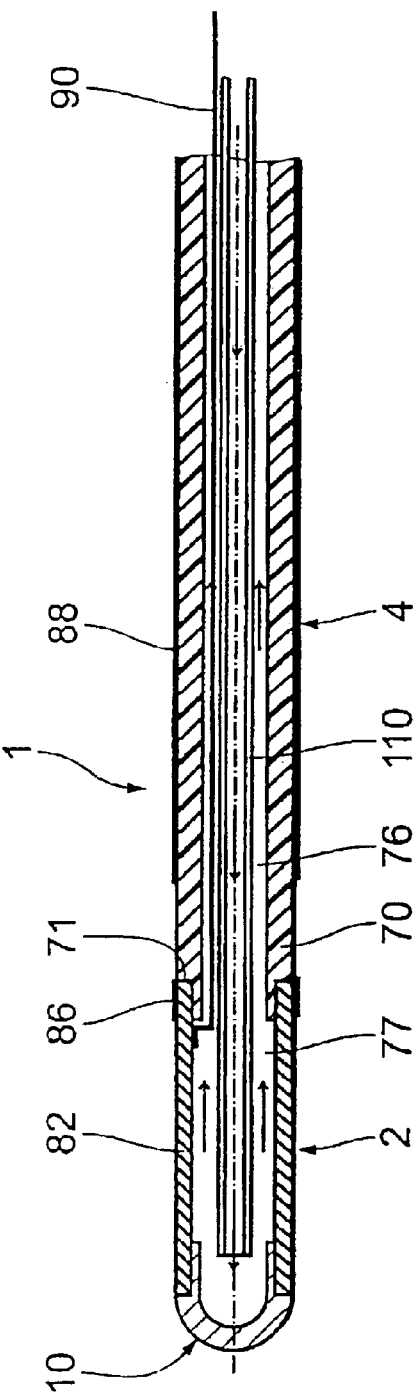
Fig. 22
Fig. 23

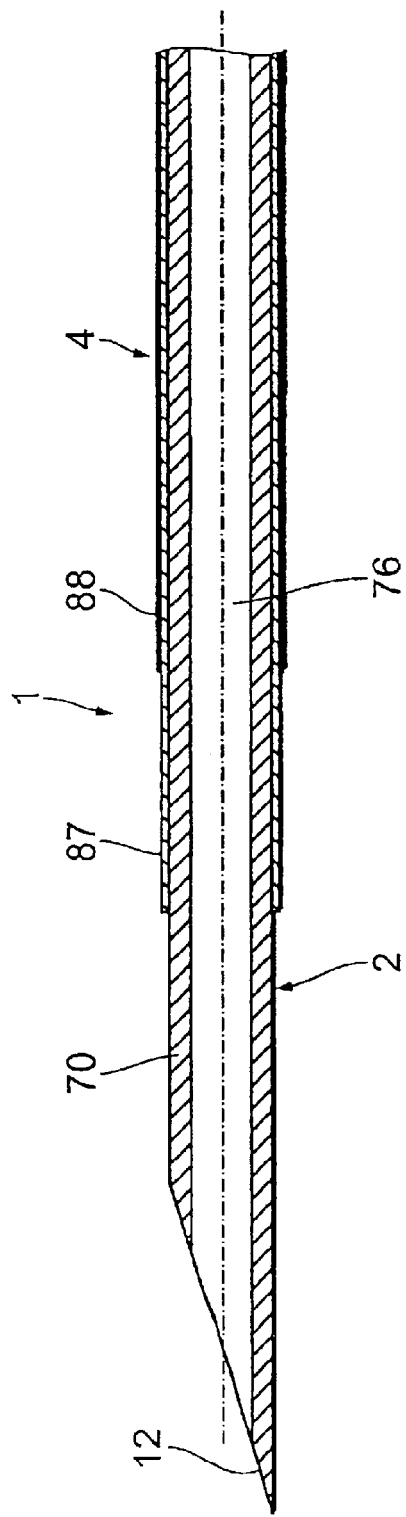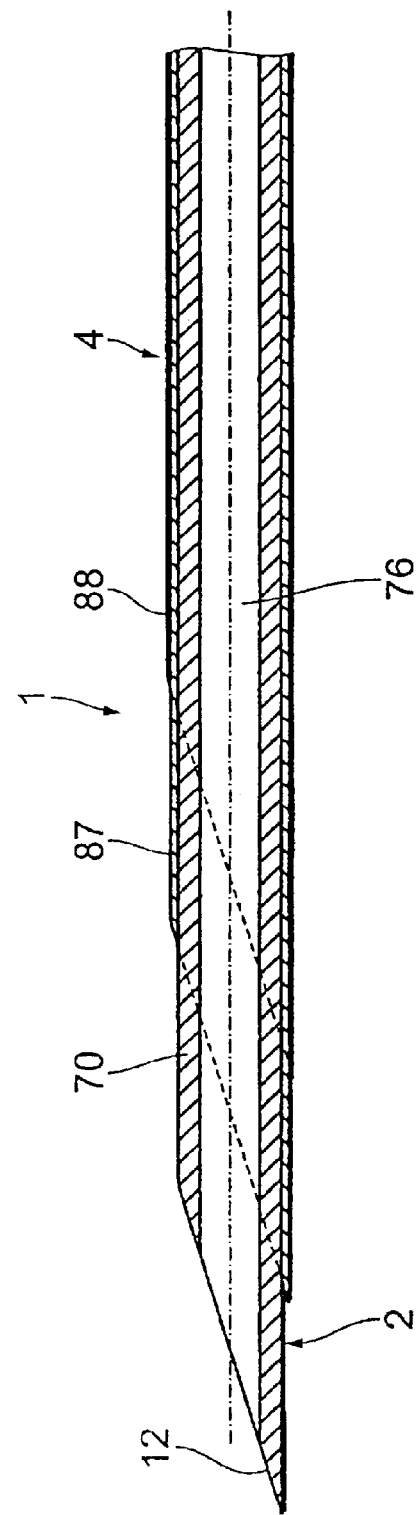

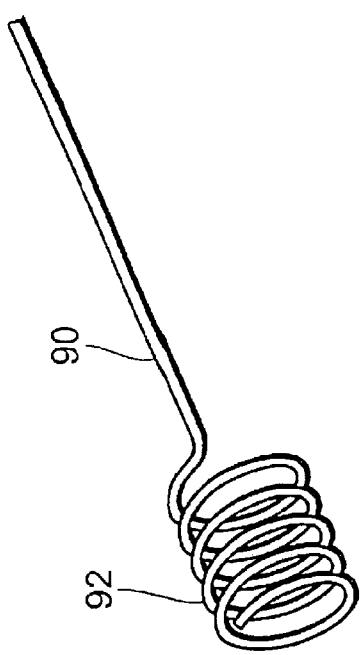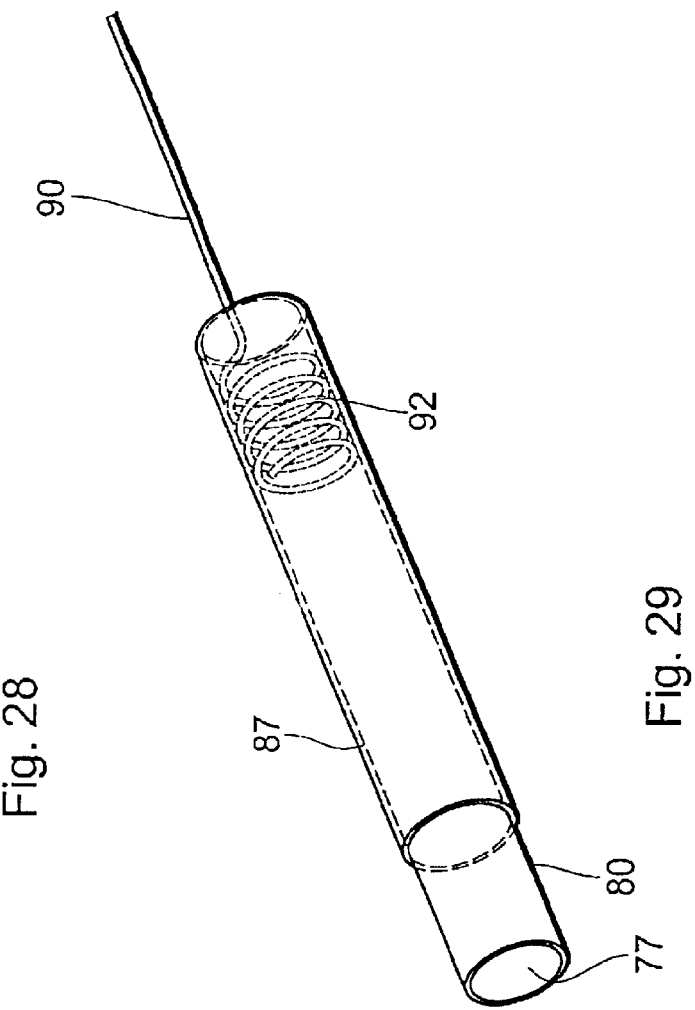

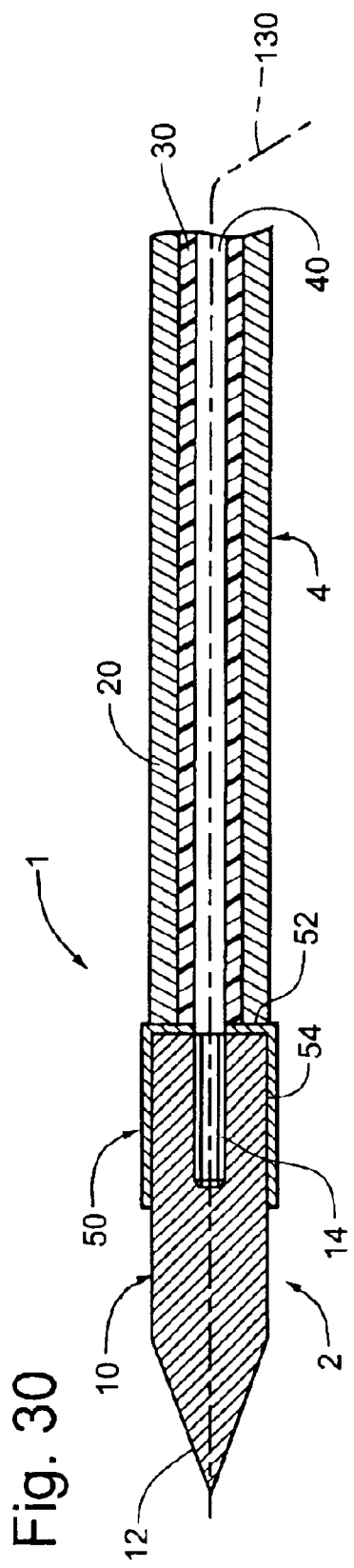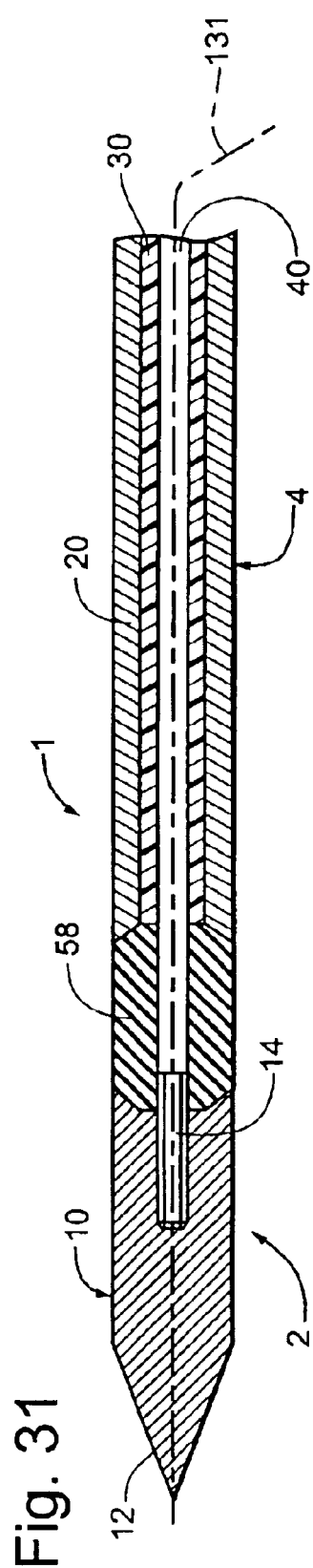

ELECTRODE ASSEMBLY FOR A SURGICAL INSTRUMENT PROVIDED FOR CARRYING OUT AN ELECTROTHERMAL COAGULATION OF TISSUE

The invention concerns an electrode arrangement for a surgical instrument for electrothermal coagulation of tissue, which includes a front cylinder at the distal end of the instrument having a distal tip, a carrier proximally adjoining the front cylinder, and two electrodes which are connectable to an ac voltage source.

Using the application of high-frequency alternating currents (for example in the frequency range of between 300 KHz and 2 MHz) to generate high temperatures for tissue coagulation and for tissue division has long been known in surgery. In a practical context, so-called monopolar electrode arrangements or bipolar electrode arrangements are used for introducing the HF-current into the tissue.

In the case of the monopolar arrangements, an electrode—also referred to as the neutral electrode—is applied in the form of an electrode of large area to the skin of the patient in the proximity of the treatment location and fixed there and earthed or connected to ground. A second electrode which is manipulated by the operator—also referred to as the active electrode—is connected to the ac voltage source. In terms of its shape, the electrode is so adapted to the respective use, in particular the size of the tissue area to be treated, that both the operational time and also the thermal loading of the region of the body or organ involved are reasonable and they coagulate only the desired area of tissue.

In the case of arrangements for bipolar HF-thermotherapy, both electrodes are connected to an HF-generator and arranged with dimensions which are fixed with respect to each other, for example on an insulating carrier, and are placed by the operator in the immediate proximity of the treatment location and generally also actively guided.

WO 97/17009 discloses a bipolar electrode arrangement with a fluid duct by way of which flushing fluid can be introduced into the operational area. Two or three electrodes are arranged in the form of a cone portion on a conical distal tip of the instrument which can be introduced into the tissue, wherein the electromagnetic HF-field is formed between the electrodes and is intended to coagulate the surrounding tissue.

WO 96/34569 and the documents referred to in the associated international search report disclose systems and processes for the coagulation of body tissue while maintaining a pre-calculated maximum tissue temperature, in which fluid cooling or thermoelectric cooling is provided during the actual tissue coagulation procedure. Those known arrangements are intended for the introduction into body cavities by way of natural accesses.

U.S. Pat. No 4,832,048 as well as WO 95/10320 and WO 99/11186 or EP 96 945 879.3 and WO 98/19613, WO 96/18349 and WO 81/03272 also disclose surgical instruments which treat tissue by means of HF-thermotherapy by means of a bipolar electrode arrangement.

The known surgical instruments for bipolar HF-thermotherapy are often expensive to manufacture and, for the various areas of use involved, they often suffer from disadvantages which frequently result in locally inaccurate tissue treatment which in particular in part does not reach the tissue to be treated or thermally overloads sound tissue.

Therefore the object of the present invention is to develop an electrode arrangement for a surgical instrument of the kind set forth in the opening part of this specification, such that it is simple to manufacture and use and permits precise localizable treatment of the tissue, while at the same time sparing surrounding sound tissue.

That object is attained by an electrode arrangement for a surgical instrument for thermoelectric coagulation of tissue, including an electrically conductive front cylinder at the distal end of the instrument, with a distal tip and with a cylindrical first electrode, a tubular outer conductor proximally adjoining the front cylinder and with a cylindrical second electrode, an insulator element between the front cylinder and the outer conductor, wherein the electrodes are connectable to an ac voltage source, characterised by a bar-shaped inner conductor in the outer conductor and an insulating tube between the inner conductor and the outer conductor.

The advantages of the invention are in particular that the electrode arrangement is of a particularly simple structure, wherein more specifically the front cylinder forms an electrode and that the proximally adjoining outer conductor which is insulated by way of an insulator element forms the second electrode so that the ac voltage source is connectable to the front cylinder and from the outside directly to the outer conductor by way of the bar-shaped inner conductor which is separated by an insulating tube outer conductor.

The insulating element has between the front cylinder and the outer conductor a radial partition which at the outside goes into a cylindrical casing wall which surrounds the front cylinder and/or the outer conductor in closely fitting relationship therewith over a predetermined axial lengthwise portion. The inner conductor is connectable to the front cylinder through that partition of the insulating element. Preferably, embodied between the front cylinder and the inner conductor is a releasable screw connection in which the inner conductor carries at its distal end a male screwthread which can be screwed to a corresponding axial female screwthread in the front cylinder. The advantages of this embodiment are in particular that the cup-like insulator element can be applied in the form of an insulating layer directly to the metal front cylinder and/or the metal outer conductor, in such a way that the separating surface between the front cylinder and the outer conductor and a lengthwise portion, axially adjoining same, of the outside surface has a coating with an insulating material. A coating of that kind can be produced for example in accordance with the invention by anodization of the surfaces in question in an electrolyte bath if the front cylinder and/or the outer conductor comprise an anodizable metal, for example titanium or aluminum.

Depending on the respective purpose of use the electrode arrangement for an instrument can be of a flexible nature so that in that case the inner conductor, the outer conductor, the insulating tube and possibly also the insulator element comprise an elastic material. In the case of a flexible surgical instrument of that kind, the bipolar electrode arrangement can under some circumstances be more easily moved to the specific treatment location. Alternatively however the inner conductor and the outer conductor can be of a straight and rigid configuration, in which case then the front cylinder and the outer conductor are arranged in mutually coaxially aligned arrangement and can then be moved to the treatment location by a rectilinear translatory movement. In regard to certain treatment locations it may also be particularly advantageous to angle the instrument in the lengthwise direction.

In all embodiments the outer conductor and the front cylinder are of substantially the same outside diameter in order to provide for unimpeded sliding movement of the electrode arrangement in the tissue.

Preferably the front cylinder, over its axial lengthwise portion which is not covered by the insulator element, forms the first electrode and the outer conductor, over the entire axial lengthwise portion, insofar as same is not covered by the insulator element, forms the second cylindrical electrode. The axial length of the electrodes is preferably greater than the axial length of the insulator element and it is also greater than the outside diameter of the front cylinder and the outer conductor. Preferably the length of the outer conductor is a multiple of the length of the front cylinder. If, in this embodiment, the tissue adjoining the outside surface of the instrument is coagulated and as a result becomes of high resistance, then in this embodiment of the invention the electromagnetic field can be displaced outwardly into adjoining tissue regions because there is a suitably long second electrode so that, if the tissue has become of high resistance adjoining the outside surface, the electromagnetic field can move radially outwardly and in so doing still ends at the second electrode. With this embodiment therefore it is possible to implement a coagulation effect which moves in a defined fashion into the tissue and which comes to an end when the field extends from the first electrode to the proximal end of the second electrode.

Conversely it has been found that the commencement of coagulation is optimal when the two electrodes are at a relatively small axial spacing from each other, which is approximately of the order of magnitude of the outside diameter or only slightly larger.

In a preferred embodiment of the invention the inner conductor and the front cylinder are provided with a central hollow duct which issues from the distal tip of the front cylinder and which contains an optical waveguide which can be acted upon with visible laser light. In that way light can be passed to the tip of the applicator. If then for example that applicator is inserted into thin-walled regions of the body, for example in the nasal concha for therapy of concha hyperplasia, then the light issuing at the tip makes it possible to locate the position of the tip in the nasal concha by the doctor implementing the treatment using the naked eye. The doctor can therefore see at any time where the tip of the electrode arrangement is disposed, in the nasal concha. The above-described surgical instrument is suitable for dynamic use, for example it is inserted into the enlarged nasal concha and then, with HF-power activated, withdrawn from the nasal concha, thereby producing a tubular coagulation zone which has formed around the path of the electrode arrangement.

In accordance with a further preferred embodiment of the invention, the front cylinder which is electrically connected to the inner conductor and the outer conductor are separated from each other by an insulating annular body. Preferably the insulating annular body is made from translucent or partially translucent material and disposed in the annular body is a light source which discharges its light to the exterior through the annular body, preferably in the form of stray or scattered light. In accordance with a preferred embodiment of this instrument the inner conductor has a hollow duct which terminates in the insulating annular body and which accommodates an optical waveguide. In the region of the annular body radially into the fiber core of the optical waveguide the inner conductor is provided with incisions so that light issues radially at the incisions from the optical waveguide and, through the annular body, makes that zone of the bipolar electrode arrangement which is between the two electrodes and in which therefore coagulation of the tissue respectively occurs, visible to the doctor carrying out the treatment. In the case of thin-walled bodies therefore the doctor performing the treatment always sees directly with his own eyes that location at which coagulation is taking place. It is thereby possible to treat the tissue in a particularly accurate and local fashion. Depending on the requirements involved the tip of the front cylinder may be conical or wedge-shaped.

The object of the invention is further attained by an electrode arrangement for a surgical instrument for electrothermal coagulation of tissue, including a front cylinder at the distal end of the instrument with a distal tip, an elongate, electrically insulating carrier proximally adjoining the front cylinder, at least two spaced electrodes on the carrier, which are connectable to an ac voltage source, characterised in that the electrodes are of a strip-shaped configuration and extend along the carrier.

The advantages of the invention lie in particular in the simplicity of structure and the electrodes which extend in a strip-shaped configuration along the carrier. Particularly when the two electrodes extend parallel to the longitudinal axis of the carrier, this electrode arrangement is suitable for therapy in respect of concha hyperplasia. The applicator, that is to say the electrode arrangement, is used statically in that case, in other words, the electrode arrangement is pierced into the enlarged nasal concha and remains fixed in a position with active HF-power. In that procedure, due to the specific electrode configuration involved, the desired tubular coagulation zone is produced without the need to move the applicator in the tissue. A further advantage is the particularly simple structure which makes it possible to implement connection of the HF-generator at the proximal end of the carrier directly—from the exterior—to the electrodes.

If the electrodes extend parallel to the longitudinal axis of the carrier and for example are disposed in mutually diametrally opposite relationship on the preferably circular carrier cross-section, then the result is two coagulation zones extending in the longitudinal direction, between the two electrodes. If in contrast the electrodes are disposed on the carrier along spaced helical lines, then a correspondingly helical zone of the tissue is treated and coagulated. In the event of an additional axial movement of the electrode arrangement, a circular coagulated enclosing passage is then formed around the carrier.

In accordance with a particularly preferred embodiment of the invention the carrier is in the form of a metal tube carrying an externally disposed insulating layer on which the strip-shaped electrodes are disposed. If the metal tube used comprises a metal which can be anodically oxidized in an electrolysis bath, for example therefore titanium or aluminum, then production of the insulating carrier is particularly simple, more specifically if the outside surface of the carrier is electrolytically anodized to form a layer of titanium oxide or aluminum oxide. In this embodiment also it is possible to draw through a hollow duct which passes axially through the carrier and issues at the tip of the front cylinder, an optical waveguide which makes the position of the tip of the front cylinder visible to the operator—when dealing with correspondingly thin tissue—or in the event of implementing a treatment just under the skin, whereby the operator can guide the arrangement in properly targeted fashion. The optical waveguide can be supplied for example with visible laser light. The distal tip of the front cylinder is advantageously either of a conical or a wedge-shaped configuration and the electrodes are applied in the form of thin conducting metal layers to the carrier.

In accordance with a preferred embodiment of the invention the carrier can be made from a flexible material on which the strip-shaped electrodes are carried. The carrier used can be for example an optical waveguide, on the insulating outer sheath of which the electrodes are disposed elastically and in a strip-shaped configuration. The electrode arrangement can then more easily be introduced through body openings to the treatment location.

In this embodiment also the axial length of the electrodes is preferably greater than the outside diameter of the front cylinder and carrier which are both preferably of the same outside diameter in order to permit the electrode arrangement to be easily introduced by a sliding movement into the tissue.

The object of the invention is further attained by an electrode arrangement for a surgical instrument for electrothermal coagulation in the tissue, including a front cylinder of metal or insulating material at the distal end of the instrument, the front cylinder is frontally pointed or rounded-off, an elongate carrier proximally adjoining the front cylinder, two electrodes which extend in the longitudinal direction of the carrier and which are connectable to an ac voltage source, characterised in that the carrier includes externally disposed, self-supporting metal bar profile members which extend in the longitudinal direction and which are connected together by means of one or more insulating spacer elements and form the electrodes.

The advantages of the last-mentioned embodiment of the invention are in particular that the electrodes extend in the longitudinal direction of the carrier and are self-supporting metal bar profile members forming the carrier, whereby manufacturing steps can be omitted in manufacture of the electrode arrangement. In a particularly preferred configuration the one or more insulating spacer elements between the electrodes is or are optical waveguides which are guided in the longitudinal direction between the bar profile members and give off light to the distal tip of the instrument so that the operator can at any time locate the tip of the instrument by visual means when the instrument is used in thin-walled parts of the body. In a particularly preferred feature the externally disposed visible optical waveguides can also be provided with radial countersinks or incisions ground therein, which provide that light also issues radially at those locations. That accordingly shows the operator over what axial distance the instrument—with HF-energy activated—is also coagulating tissue. The cross-section of the bar profile members corresponds, when considered together, preferably to a circular surface area, but alternatively the cross-section of the bar profile members can also be in the form of a portion of the periphery of a tube, in which case then the bar profile members are for example preferably fixed in mutually opposite relationship on the outside sheath of an optical waveguide and in that way form a rigid carrier with externally disposed strip-shaped electrodes extending in the longitudinal direction.

The object of the invention is further attained by an electrode arrangement for a surgical instrument for thermoelectrical coagulation in tissue, including a front cylinder of metal or insulating material at the distal end of the instrument, wherein the front cylinder is frontally pointed or rounded-off, an elongate carrier proximally adjoining the front cylinder, and two electrodes which extend in the longitudinal direction of the carrier and which are connectable to an ac voltage source, characterised in that the electrodes (2, 4) are cylindrical tube portions (82, 84) of metal which are arranged at a predetermined spacing from each other in axial alignment with the carrier in the longitudinal direction.

In accordance with this preferred embodiment of the invention the first electrode can be in the form of a self-supporting tube portion which is carried between the front cylinder and an insulating tubular first carrier and the second electrode can also be in the form of a self-supporting tube portion arranged between the first carrier and a second tubular carrier, wherein the end portions of the electrodes are supported on the front cylinder, the first and the second carrier over a predetermined lengthwise portion. Alternatively it is also possible for the second electrode to extend as far as the proximal end portion. Particularly preferably in this embodiment the lengthwise portions of the electrodes which bear on the first and/or the second carrier are covered with an insulating layer. In addition, provided within the hollow duct is a flushing tube which extends from the proximal end of the instrument to the front cylinder, that is to say also through the tube portions which form the electrodes, and extends as far as the front cylinder and discharges fluid at the distal end into the hollow duct in which the fluid—in contact with the electrodes—flows back to the proximal end of the instrument.

Cooling of the electrode surfaces by means of a flushing fluid means that the so-called "hot-spot" of coagulation is displaced by approximately between two and three millimeters from the surface of the instrument into the tissue. The cooling action ensures that the tissue-electrode contact surface is always kept below a predetermined temperature and therefore does not dry out to such a severe degree, so that the introduction of energy into the adjoining tissue is also guaranteed, over a relatively long period of time. It is quite particularly advantageous in that respect that the lengthwise portions of the electrodes which rest on the insulating carriers—or in a specific embodiment also on the front cylinder which is in the form of an insulating body—and are therefore not directly cooled by the cooling fluid, are covered with an insulating layer. In that way those lengthwise portions which are cooled to a lesser degree and which consequently heat up to a greater degree than the cooled electrode portions are covered over by the insulator and therefore come into contact with the adjoining tissue only by way of the comparatively cooler insulating layer. Thus, the consequence of covering over the end portions of the electrodes, which are not cooled by the flushing fluid, by means of insulating layers, is that the adjoining tissue does not become too hot even in those longitudinal portions, and thus it does not dry out.

In a preferred embodiment of the invention a self-supporting metal tube is provided between the front cylinder and the carrier. A distal portion of the metal tube serves as the first electrode, an adjoining proximal tube portion is surrounded by a cylindrical insulating layer and carries on that insulating layer a metal layer which serves as the second electrode. Alternatively, the proximal tube portion may also be used as the second electrode and then disposed on the distal tube portion is a cylindrical insulating layer which is coated with a metal layer, wherein that distal metal layer then serves as the first electrode.

This embodiment of the invention has the advantage of affording ease of manufacture and assembly of the bipolar electrode arrangement. This applies in particular when the metal used is an anodizable material, for example titanium or aluminum and the cylindrical insulating layer applied to the tube portion is produced by anodic oxidation (anodization) of the metal surface, in which case the metal layer deposited thereon can be produced for example by vapor deposition or electrolytic coating. In this embodiment the carrier has a hollow duct which is extended into a hollow duct through the metal tube. The connecting lines for the electrodes extend from the electrodes through the hollow duct to the proximal end of the instrument. In accordance with the invention this preferred embodiment thereof also provides that a flushing tube is taken through the hollow duct, which extends as far as the front cylinder and discharges cooling fluid at the distal end into the hollow duct.

Advantageously, provided as a prolongation of the hollow duct of the carrier in the front cylinder is an opening in which there is disposed a temperature sensor whose connecting line is passed through the hollow duct to the proximal end of the instrument. In that way it is possible—for example for therapy in respect of benign prostate hyperplasia to fit a temperature sensor or thermistor into the tip of the front cylinder, which can be used to measure the tissue temperature. Preferably the carrier is formed from a flexible insulating hoze or tube and the electrodes are cylindrical self-supporting tube portions of metal which are fixed at predetermined spacings on the carrier. In this embodiment of the invention the outside diameter of the front cylinder also corresponds to the outside diameter of the electrodes and the axial length of the electrodes is greater than the diameter, while the axial spacing of the two electrodes from each other is approximately equal to or smaller than the outside diameter thereof. It has been found that, with that dimensioning, the electrical field which causes coagulation of the tissue can be sufficiently strongly produced and also—after the tissue adjoining the outside surface is coagulated—can be propagated sufficiently far into the tissue so that an advantageous large coagulation zone is produced.

The temperature sensor in the opening in the front cylinder is preferably embedded in synthetic resin or in an adhesive bed which provides for good conduction of the temperature of the metal front cylinder to the temperature sensor. The outside diameter of the electrodes and the outside diameter of the front cylinder are identical and the intermediate space between the electrodes is filled with insulating material so that this lengthwise portion is also of the outside diameter which occurs elsewhere. That provides for a uniform cross-section over the distal tip to the proximal end of the second electrode, in contrast to which the flexible carrier, adjoining same, can be of a reduced outside diameter. The consequence of the constant dimension of the outside diameters in the region of the front cylinder and the electrodes is that the instrument can be introduced into the tissue easily and in particular without impediment.

The object of the invention is further attained by an electrode arrangement for a surgical instrument for electrothermal coagulation of tissue, including a front cylinder of metal at the distal end of the instrument, an elongate cylindrical carrier proximally adjoining the cylinder and comprising insulating material, two spaced cylindrical electrodes, characterised in that the metal front cylinder is rounded-off at the distal end and adjoining the round end portion has a cylinder portion of predetermined length, that the front cylinder forms the first electrode, and that a metal layer as the second electrode is disposed on the carrier at a predetermined axial spacing from the front cylinder.

In this preferred embodiment of the invention, extending through the carrier is a hollow duct which is extended into the front cylinder and which accommodates a flushing hoze or tube which at its distal end discharges flushing fluid which flows back along the inside wall of the front cylinder and finally between the carrier and the flushing tube to the proximal end.

The front cylinder can be fixed with its proximal end in an annular opening in the carrier and the overlap region between the carrier and the front cylinder has on its outside an oxide layer on the metal front cylinder, which ensures that the metal of the front cylinder which is uncooled at that location does not come into contact in an overheated condition with the adjoining tissue.

The carrier can be of both a flexible and a rigid nature and, as the front cylinder is formed from metal material, this instrument—by virtue of the active tip—makes it possible to treat edge tumors which are disposed immediately in front of the rounded-off front cylinder. A prerequisite for advantageous functioning of this electrode arrangement is that the dissipation of heat by the cooling circulation is as far as possible the same at both electrodes. That is achieved if the mean current density at the first, that is to say distal electrode is greater than or equal to the current density at the second, proximal electrode. That condition is met when the surface area $A_1$ of the first electrode is smaller than or equal to the surface area $A_2$ of the second electrode. Insofar as the surface area component of the round end portion—with its radius R—is also taken into consideration, that gives the following relationship in respect of the lengths $L_1$, $L_2$ of the first and second electrodes: $L_1+R \leq L_2$. If very great lengths $L_2$ of the second electrode are to be implemented and if nonetheless the degree of flexibility of the applicator is to be maintained, then the second electrode can be constructed by coating the flexible carrier with a metal layer.

The object of the invention is further attained by an electrode arrangement for a surgical instrument for electrothermal coagulation of tissue including: an elongate cylindrical carrier comprising a metal tube or a metal bar, two spaced cylindrical electrodes on the carrier, characterised in that the first electrode is a distal portion of the carrier, that on a portion axially adjoining same an insulating layer is applied to the carrier, and that a cylindrical metal layer as the second electrode is arranged on the insulating layer at a predetermined axial spacing from the first electrode.

In this embodiment of the invention the front cylinder and the carrier are embodied in the form of an integral metal tube or metal bar whose distal end is pointed. A distal portion of the metal tube or metal bar forms the first electrode. Adjoining same, an insulating layer is applied to the carrier and then a cylindrical metal layer is deposited on the insulating layer in the proximal region of the insulating layer and forms the second cylindrical electrode. The insulating layer can be embodied by a plastic hoze or tube to which a metal coating is applied, as the second electrode. The metal carrier with the distal tip represents a bipolar electrode arrangement in the form of a cannula or needle and is suitable in particular for therapy in respect of enlarged terminal vessels such as for example finely mottled varicose veins. The electrode arrangement is pierced with its tip in the longitudinal direction into the enlarged vessel. Upon activation of the HF-power the blood and the vessel wall coagulate primarily around the first electrode. When that happens the vessel contracts so as to afford a closure effect with the result than then no further blood can flow into the vessel whereby the vessel is no longer perceptible through the skin and the desired cosmetic effect is achieved.

It is particularly advantageous to employ insulating layers which are used in bipolar electrode arrangements, comprising ceramic material. The advantage of this material is that it has a high level of mechanical strength and can be easily produced by means of electrolytic anodization (eloxation) for example on titanium in the form of titanium oxide or in the case of aluminum in the form of aluminum oxide. The thickness of the layer depends on the electrical voltage used in the electrolysis operation. Instead of titanium, various titanium alloys on which the ceramic layer is produced by anodic oxidation are also suitable as the starting material involved. In order to implement complete or partial coating in that way with titanium or suitable titanium alloys or aluminum, firstly the corresponding metal body is subjected to a preliminary chemical cleaning operation in order to obtain grease-free and oxide-free surfaces. Then, the places which are not to be coated are masked. Masking can be effected by means of special lacquers or layers but also by shrink tubes. For anodically applying a ceramic layer, the starting material, that is to say titanium, titanium alloys or aluminum is to be electrically contacted and subjected to voltage as the anode.

In order for example—based on titanium as the starting material to apply a titanium oxide ceramic layer, the following steps are to be taken: in order to convert the titanium at its surface into its ion phase, a suitably molar acid in aqueous solution is to be used. The molar solutions in question are between 0.1 and 1 molar $H_2SO_4$ (sulfuric acid) and $H_3PO_4$ (phosphoric acid) respectively. By the application of a suitable dc voltage, oxygen is deposited at the electrode, the titanium electrode which is to be coated in this case, and bonds to the ionized titanium surface and is converted to titanium oxide. Depending on the respective layer thickness involved, the dc voltages and currents to be used are between 10V and 500V at maximum currents of 1A. As a result the oxidation procedure passes through a plurality of oxidation stages (titanium oxides) depending on the respective length of the procedure. The layer thicknesses which are to be achieved with these processes are of the order of magnitude of between 20 and 30 $\mu m$. By means of the layer thicknesses which are to be represented by way of interference colors, due to the differing light refraction at the interface with the metal (the oxide layer is transparent), the latter can be represented proportionally over a color spectrum. With that method it is possible efficiently to provide specific paramagnetic electrodes of titanium—or titanium alloys such as $TiAl_6V_4$—with a dielectric ceramic layer, being variable in terms of layer thickness and/or color.

Besides the good dielectric properties of the ceramic layers produced in that way, the tribological properties are also excellently well suited to possibly increasing the levels of abrasion strength and surface quality. These colored ceramic layers are also suitable for the stable marking of needles, cannulae or probes. A proportional interference color is to be selected by way of the choice of the layer thickness. It is possible in that way to set colors of grey, gold, violet and on to blue.

In accordance with a further preferred embodiment of the invention at least one of the connecting lines which serve to connect the electrodes has at its end a portion of spring metal, preferably spring wire, which is of such a configuration that it is clamped in the hollow duct—within the electrodes—radially outwardly against the inside surface of the electrodes and thereby sufficiently reliably and securely produces electrical contact. The spring metal portion of the connecting lines of that configuration is preferably wound to form a spiral or coil spring which is acted upon by a predetermined tensile stress in the spiral wire, the winding of which therefore under that tensile stress is of a reduced diameter so that it can be easily introduced from the exterior into the cavity of the electrode. The tensile stress acting on the spring wire is then removed, the spiral spring then attains its full outside diameter and in so doing bears in self-clamping relationship from the interior against the inside surfaces of the electrodes. In order easily to be able to implement introduction of the corresponding spring portions at the end of the connecting lines, it is possible to use a corresponding special tool which makes it possible to insert the spiral spring of reduced diameter, then remove the tensile biasing of the spiral spring wire, and thus cause the spiral spring to bear against the inside surface of the electrode.

Advantageous developments of the invention are characterised by the features of the appendant claims.

Embodiments of the invention are described in greater detail hereinafter with reference to the drawing in which:

FIG. 1 is a view in longitudinal section through a first embodiment of a bipolar electrode arrangement for a surgical instrument, FIG. 2 is a view in longitudinal section through a second embodiment of a bipolar electrode arrangement, FIG. 3 is a view in longitudinal section through a third embodiment of a bipolar electrode arrangement, FIG. 4 is a view in longitudinal section through a fourth embodiment of a bipolar electrode arrangement, FIG. 5 is a view in longitudinal section through a fifth embodiment of the bipolar electrode arrangement, FIG. 6 is a view in longitudinal section through a sixth embodiment of the bipolar electrode arrangement, FIG. 7 is a view in longitudinal section through a seventh embodiment of the bipolar electrode arrangement, FIG. 8 is a view in cross-section through the seventh embodiment, FIG. 9 is a view in longitudinal section through an eighth embodiment of the bipolar electrode arrangement, FIG. 10 is a view in cross-section through the eighth embodiment, FIG. 11 is a view in longitudinal section through a ninth embodiment of the bipolar electrode arrangement, FIG. 12 is a view in cross-section through the ninth embodiment, FIG. 13 is a view in cross-section through a tenth embodiment of the bipolar electrode arrangement, FIG. 14 is a view in cross-section through an eleventh embodiment of the bipolar electrode arrangement, FIG. 15 is a side view of a twelfth embodiment of the bipolar electrode arrangement;

FIG. 16 is a view in longitudinal section through the twelfth embodiment,

FIG. 17 is a view in longitudinal section through a thirteenth embodiment of the bipolar electrode arrangement with a pointed front cylinder of insulating material, FIG. 18 is a view in longitudinal section through the thirteenth embodiment with a metal pointed front cylinder, FIG. 19 is a view in longitudinal section through the thirteenth embodiment with a metal frontally rounded-off front cylinder, FIG. 20 is a view in longitudinal section through a fourteenth embodiment of the bipolar electrode arrangement, FIG. 21 is a view in longitudinal section through a fifteenth embodiment of the bipolar electrode arrangement, FIG. 22 is a view in longitudinal section through a sixteenth embodiment of the bipolar electrode arrangement, FIG. 23 is a view in longitudinal section through a seventeenth embodiment of the bipolar electrode arrangement, FIG. 24 is a view in longitudinal section through a eighteenth embodiment of the bipolar electrode arrangement, FIG. 25 is a view in longitudinal section through an alternative form of the eighteenth embodiment, FIG. 26 is a view in longitudinal section through a second alternative form of the eighteenth embodiment, FIG. 27 is a perspective view of a front cylinder with a partial coating with ceramic material, FIG. 28 shows an end portion of a connecting line for the connection of an electrode, and FIG. 29 is a perspective view of an electrode formed from a metal tube with a ceramic coating and a connecting line disposed in the interior of the tube.

FIG. 30 is a view in longitudinal section through another embodiment of a bipolar electrode arrangement for a surgical instrument where the instrument extends angled in the longitudinal direction.

FIG. 31 is a view in longitudinal section through still another embodiment of a bipolar electrode arrangement for a surgical instrument where the instrument extends angled in the longitudinal direction.

Figure 15:
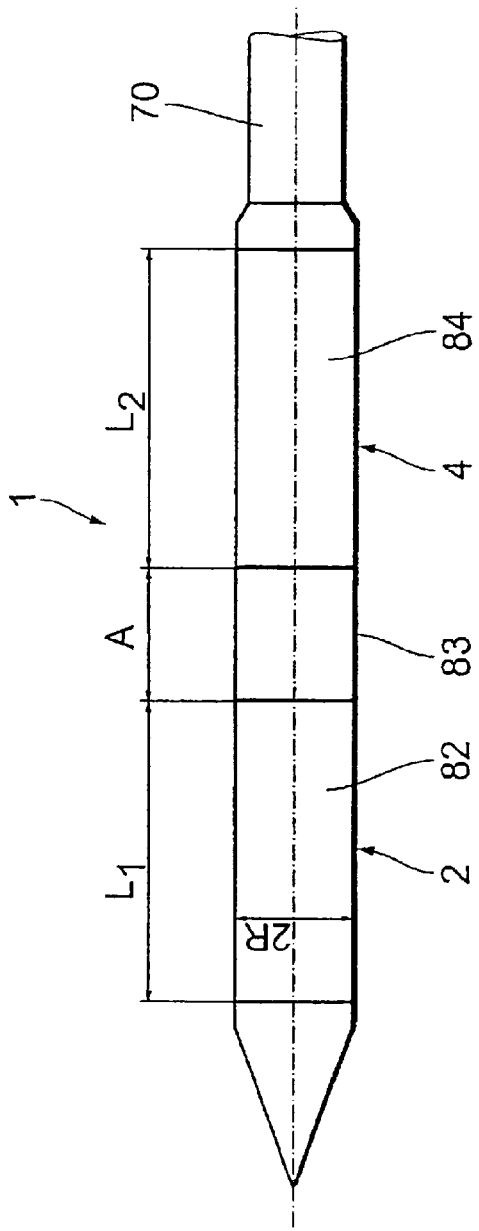

FIG. 1 shows a longitudinal section through a first embodiment of a bipolar electrode arrangement, which is a component of a surgical instrument for the electrothermal coagulation of tissue. The electrode arrangement includes an electrically conductive front cylinder 10 which forms the distal end of the instrument, that is to say the end which is remote from the user of the instrument. The front cylinder terminates at its free end in a point 12 which in the illustrated embodiment terminates in a conically pointed configuration. Adjoining the front cylinder 10 is a tubular outer conductor 20 which in its interior accommodates an insulating hoze or tube 30 through which extends a bar-shaped inner conductor 40. At its distal end the bar-shaped inner conductor 40 has a male screwthread which can be screwed into a corresponding female screwthread extending in the axial longitudinal direction and is electrically and mechanically connected to the front cylinder 10 by means of that screw connection 14.

Arranged between the front cylinder 10 and the outer conductor 20 is an insulator element 50 which has a radial partition 52 between the front cylinder 10 and the distal end wall of the outer conductor 20 and the insulating tube 30. At the outside on the partition 52 the insulator element 50 goes into a casing wall 54 which—in the illustrated embodiment—surrounds the outside surface of the front cylinder 10 in a condition of bearing snugly thereagainst but which in an alternative embodiment—directed towards the proximal end—can also surround the outside surface of the outer conductor 20. The exposed outside surface of the front cylinder 10 forms a first electrode 2. The exposed outside surface of the outer conductor 20 forms a second electrode 4. A high-frequency ac voltage source is connected to the two electrodes—at the proximal end of the electrode arrangement—when the bipolar electrode arrangement is introduced into the human or animal tissue to be treated and the tissue is to be coagulated by the thermal action of the electrical field.

FIG. 2 shows a second embodiment of the bipolar electrode arrangement according to the invention, in which once again a front cylinder 10 terminates in a conical distal tip 12, while again a bar-shaped metal inner conductor is surrounded by an insulating tube 30 which in turn is surrounded by a metal tubular outer conductor 20. Provided between the front cylinder 10 and the end wall of the outer conductor and the insulating tube 30 is an insulator element 50 which is in the form of an annular body 58 and which is of a predetermined axial length which holds the front cylinder 10 and the outer conductor 20 at a spacing. The front cylinder 10 comprises metal and serves as the cylindrical first electrode 2. The outer conductor 20 is also made from metal and serves as the cylindrical second electrode 4. The front cylinder 10 is connected to the inner conductor 40 by means of a screw connection 14. Connected to the proximal end of the electrode arrangement between the outer conductor 20 and the inner conductor 40 is an HF-ac voltage source if electrothermal coagulation of surrounding tissue is to be effected.

FIG. 3 shows an embodiment, corresponding to FIGS. 1 and 2, of a bipolar electrode arrangement in which the insulator element 50 is of a cup-shaped configuration, with the cylindrical casing wall 54 being carried in a suitable annular opening 11 in the front cylinder 10. In addition the radial partition 52 of the insulator element 50 is passed in the direction of the proximal end in a tubular configuration—at the diameter of the insulating tube 30—against the insulating tube 30 which terminates a corresponding axial length short of the distal end wall of the outer conductor 20.

FIG. 4 shows a fourth embodiment of a bipolar electrode arrangement 1 according to the invention, which substantially corresponds to the arrangement shown in FIG. 1, with the same parts being denoted by the same references. In addition to the arrangement shown in FIG. 1, extending centrally through the bar-shaped inner conductor 14 and in aligned relationship therewith and also through the front cylinder 10 is a hollow duct through which passes an optical waveguide which passes visible light to the distal tip 12 of the electrode arrangement when the optical waveguide is proximally fed for example with visible laser light. The optical waveguide 60 includes a sheath 62 surrounding the light-conducting core 64. A cladding can also be provided around the sheath 62.

FIG. 5 shows a further embodiment of the invention which substantially corresponds to the embodiment of FIG. 4, but in which the front cylinder 10 has a wedge-shaped tip 12 at its distal end. Once again, extending through the inner conductor 40 and adjoining same also through the front cylinder 10 is a central hollow duct through which an optical waveguide 60 passes with its sheath 62 and the core 64 to the distal tip 12 and optically indicates the position of the distal tip 12 in the tissue for the user of the electrode arrangement, in particular when treating tissue in thin-walled parts of the body.

FIG. 6 shows a further embodiment of the bipolar electrode arrangement 1 according to the invention, which substantially corresponds to the embodiment of FIG. 2 or FIG. 4. Provided between the front cylinder 10 and the concentric arrangement comprising the outer conductor 20, the insulating tube 30 and the inner conductor 40 is an annular body 58 through which the inner conductor 40 axially extends to the front cylinder 10. The inner conductor 40 has a central hollow duct which extends as far as the distal end of the annular body 58 and includes an optical waveguide 60. The annular body 58 is formed from transparent or semitransparent material and allows light to pass therethrough to the exterior. Formed in the inner conductor into the core 64 of the optical waveguide in the region of the annular body 58 are radial ground incisions 42, with the consequence that light issues to the exterior from those incisions radially from the inner conductor 40 and through the annular body 58 so that the position of the electrical field which is produced between the first electrode 2 and the second electrode 4 when HF-power is applied to the inner conductor 40 and the outer conductor 20 can be made optically visible to the operator. Preferably, the annular body 58 is of such a material or its surface is of such a structure that the light 3 issuing from the optical waveguide passes to the exterior in the form of stray or scattered light.

FIGS. 7 and 8 show a further embodiment of the bipolar electrode arrangement 1 according to the invention in longitudinal section and in cross-section. Proximally adjoining a front cylinder 10 having a distal tip 12 is an elongate, electrically insulating carrier 70 which—in the illustrated embodiment—is in the form of a metal tube 71 with an externally disposed insulating layer 72. For example the metal tube comprises titanium or a titanium alloy and the insulating layer 72 is produced by anodization of the surface of the tube 71 in the form of a thin ceramic layer. Applied to the insulating layer 72 are two strip-shaped electrodes 2, 4 which extend parallel to each other in the longitudinal direction of the carrier 70 and which—on the periphery of the insulating layer, see FIG. 8—are disposed in mutually diametrally opposite relationship. In the case of this electrode arrangement, an electrical field is produced in the longitudinal direction of the carrier, namely along the entire strip-shaped electrode 2, 4, so that corresponding coagulation strips are also produced in the longitudinal direction of the bipolar electrode arrangement when a corresponding HF-ac voltage source is applied to the electrodes 2, 4.

FIGS. 9 and 10 show a further embodiment of a bipolar electrode arrangement 1 for a surgical instrument according to the invention, this embodiment representing a development of the embodiment shown in FIGS. 7 and 8. An elongate, uniform, insulating carrier 70 comprises a metal tube 71 which is completely coated with an insulating layer 72 and which has continuously as far as the distal tip 12 a central hollow duct through which an optical waveguide 60 extends to the distal tip 12. The optical waveguide 60 comprises a light-conducting core 64 and a sheath 62 surrounding the core. Disposed externally on the insulating layer 72 in the longitudinal direction, that is to say in mutual parallel relationship, are two strip-shaped electrodes 2, 4 which extend over the entire illustrated length of the carrier 70 and which are fixed on the insulating layer 72.

FIGS. 11 and 12 show a further embodiment of the invention which substantially corresponds to the embodiment shown in FIGS. 9 and 10, but without using a tubular metal carrier 70. On the contrary FIGS. 11 and 12 show an embodiment in which an optical waveguide 60 with a core 64, a sheath 62 and a plastic cladding 61 is provided at its free end with a wedge-shaped tip 12 and which on the sheath or cladding 61 in the longitudinal direction has two strip-shaped electrodes 2, 4 which are arranged in mutually opposite relationship at the periphery. In this embodiment the electrodes 2, 4 are applied in the form of flexible layers so that the entire bipolar electrode arrangement is flexible.

FIGS. 13 and 14 show views in cross-section of bipolar electrode arrangements in which the carrier 70 is formed from self-supporting metal bar profile members 76 extending in the longitudinal direction. In FIG. 13 two bar profile members 76 of metal are spaced in insulating relationship by spacer elements 60. The bar profile members 76 are each approximately of a cross-sectional configuration of a semicircular area and form elongate electrodes 2, 4 which extend in the longitudinal direction of the electrode arrangement. In the illustrated embodiment the spacer elements 60 are in the form of optical waveguides 60. Preferably fitted at the side surfaces are optical waveguides at which light can also issue sideways so that, when using a bipolar electrode arrangement of that kind, the operator can see along the length of the electrodes 2 and 4 light signals which indicate the position of the electrodes 2, 4 over the length thereof.

FIG. 14 shows an embodiment which corresponds to FIG. 13 and in which two bar-shaped, self-supporting, metal bar profile members 76 which in cross-section are in the shape of portions of the wall of a tube is applied to the outer cladding of an optical waveguide in the longitudinal direction thereof and are secured in position there and form the electrodes 2, 4. In the illustrated form the optical waveguide 16 also has a sheath 62 between the outer cladding 61 and the core 64.

Figure 16:
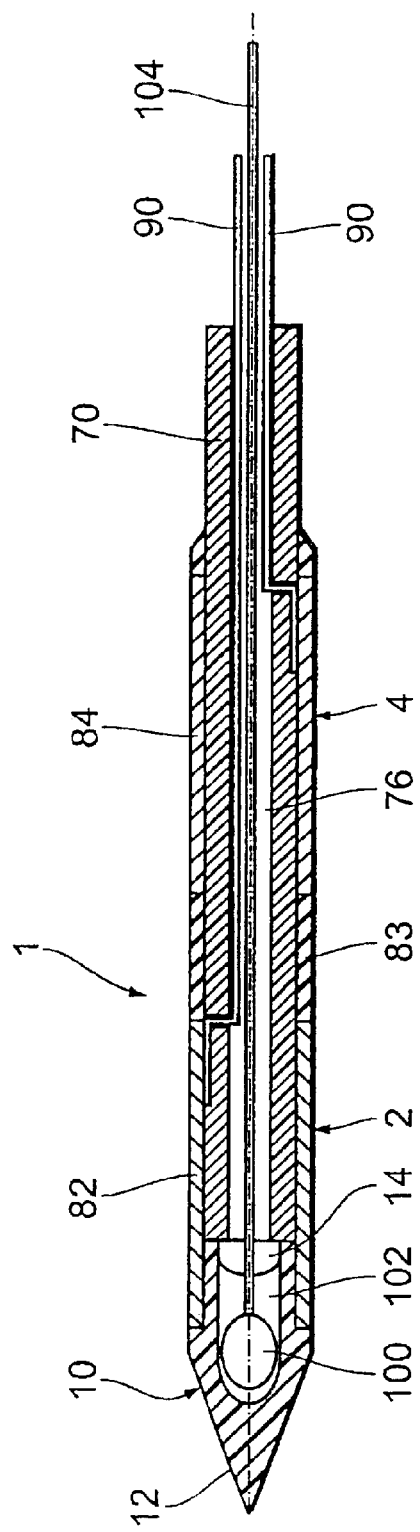

FIGS. 15 and 16 show an embodiment of a bipolar electrode arrangement in which a front cylinder 10 at the distal end of the instrument is provided with a distal conical tip 12 which is adjoined by an elongate, electrically insulating carrier 70. Two tube portions 82, 84 are pushed on the carrier 70 spaced by way of a spacer portion 83 of insulating material and secured in position there, to form cylindrical electrodes 2, 4. Extending axially through the carrier 70 is a central hollow duct 76 which communicates with an opening 14 in the front cylinder 10 and accommodates a temperature sensor 100 which is surrounded by a plastic or adhesive bed 102 and is there fixed in position and by way of a line 104 supplies a signal to the proximal end of the instrument, corresponding to the temperature of the front cylinder 10. Also provided in the hollow duct 76 are connecting lines 90 which through the carrier 70—are connected to the electrodes 2, 4 and can be connected to the proximal HF-generator.

The axial length L1 of the first electrode 2 and the axial length L2 of the second electrode 4—in all the illustrated embodiments—are greater than the spacing A between the two electrodes 2, 4. The spacing A is preferably of the order of magnitude of the outside diameter of the electrodes 2, 4. The insulating portion 83 is of the same outside diameter D=2R as the tube portions 82, 84 which form the electrodes 2, 4. R is the radius of the electrode arrangement which is generally of a circular-cylindrical configuration. In the embodiment shown in FIGS. 15 and 16 in a particularly preferred case L1=L2.

Figure 17:
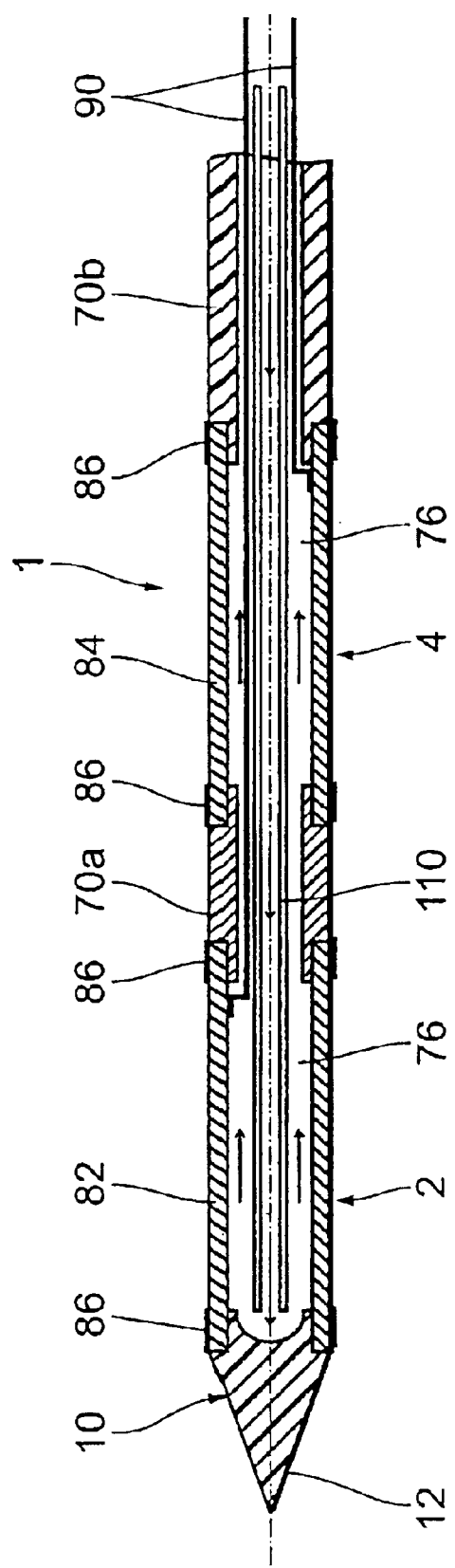

FIG. 17 shows an embodiment of a bipolar electrode arrangement in which a front cylinder 10 with a conical distal tip 12 is fixed to the end of a first tube portion 82, that first tube portion 82 being secured with an end portion to a first carrier 70a. A second tube portion 84 is carried with an end portion on the first carrier 70a and with its other end portion on a second carrier 70b. The carriers 70a and 70b each have a respective hollow duct 76, the axis of which aligns with the axis of the tube portions 82, 84. The tube portions 82, 84 represent the cylindrical electrodes 2, 4.

Extending through the hollow duct 76 of the carriers 70a and 70b and the tube portions 82, 84 is a flushing hoze or tube 110 which discharges fluid at its distal end, which then in contact with the inside wall of the tube portions 82, 84 flows back through the hollow duct 76 to the proximal end and cools the two tube portions 82, 84. At the locations where the tube portions 82, 84 are pushed over the insulating carriers 70a, 70b and over the insulating front cylinder 10 and glued fast in position at that location, the tube portions 82, 84 are provided on their outside surface with an annular insulating layer so that, at those locations which are only cooled by the fluid to a lesser degree, the electrode temperature does not experience an unwanted excessive rise which results in the tissue being undesirably baked fast to the electrodes or which results in the tissue bearing thereagainst drying out and thus causes a rise in impedance in that tissue and causes an interruption in the electrical current through the tissue.

Cooling with a suitable cooling fluid affords the consequence that the tissue at the contact surface with the electrodes does not exceed a predetermined temperature and that the coagulation hot-spot is some millimeters away from the electrodes.

FIGS. 18 and 19 correspond to the embodiment of FIG. 17, but the front cylinder 10 in FIGS. 18 and 19 comprises metal and goes directly into the first tube portion 82, the first electrode, while the front cylinder 10 in FIG. 19 is frontally rounded off. In a particularly preferred embodiment the lengths L1 and L2 of the electrodes 2, 4 are such that the surface area formed from the front cylinder 10 and the first electrode is equal to or smaller than the surface area of the second electrode.

FIG. 22 shows an embodiment of the bipolar electrode arrangement which substantially corresponds to that shown in FIG. 17, but in which the second tube portion 84 which represents the second electrode 4 is substantially longer than the first tube portion 82 which represents the first electrode 2. In this embodiment the second tube portion 84 terminates at the proximal end of the instrument and it is therefore possible to omit a further carrier at the proximal end of the instrument. The axial length of the second electrode 4 is limited by virtue of the fact that disposed on the proximal end portion of the second tube portion 84 is an insulating layer 87 which covers over the metal surface of the second tube portion 84 at that location, for example with a ceramic coating. The field which produces thermoelectric coagulation is then formed between the cylindrical metal electrodes 2, 4. In this embodiment also the end portions of the tube portions 82, 84 which on the inside are surrounded either by the insulating material of the front cylinder 10 or the insulating material of the carrier 70 are also coated with an insulating layer 86 on the outside surface in order to prevent punctiform overheating of the electrodes at those locations, because of the absence of cooling.

FIG. 23 shows a further embodiment of the invention in which a frontally rounded-off front cylinder 10 goes into a first tube portion 82 which is fixed with its proximal end to an insulating carrier. Provided at a predetermined spacing from the tube portion 82 on the insulating carrier is a metal layer 88. The tube 82 forms the cylindrical first electrode 2, the metal coating on the carrier 70 forms the cylindrical second electrode 4. The carrier 70 and the tube 82 are each provided with a central hollow duct 76 and 77 respectively through which a flushing hoze or tube 110 passes to a position just short of the distal end of the front cylinder 10, for discharging fluid at the distal end, the fluid cooling the first electrode by coming into contact with the internal surface of the first electrode 2. Disposed on the outside surface of the proximal end portion of the tube 82 is an insulating layer 86 in order to prevent local overheating of the electrode 2 at that location as that location is not in contact at the inside with fluid. The front cylinder 10 is formed from metal, its rounded configuration at the distal end is advantageously suitable for the treatment of edge tumors in which a layer of coagulated tissue is formed in front of the distal end of the instrument.

Figure 20:
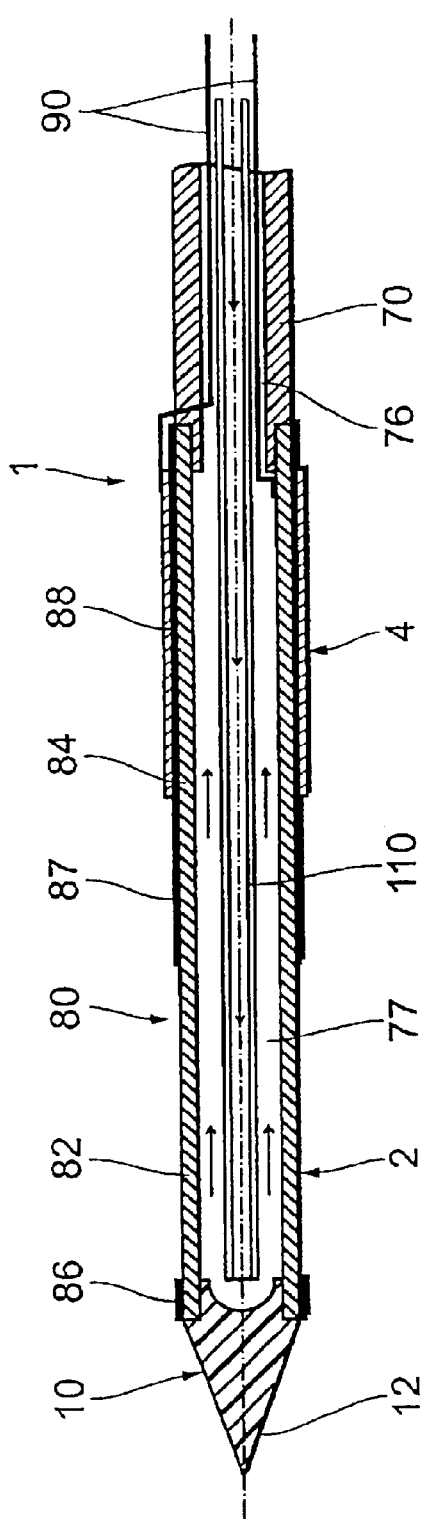
Figure 21:
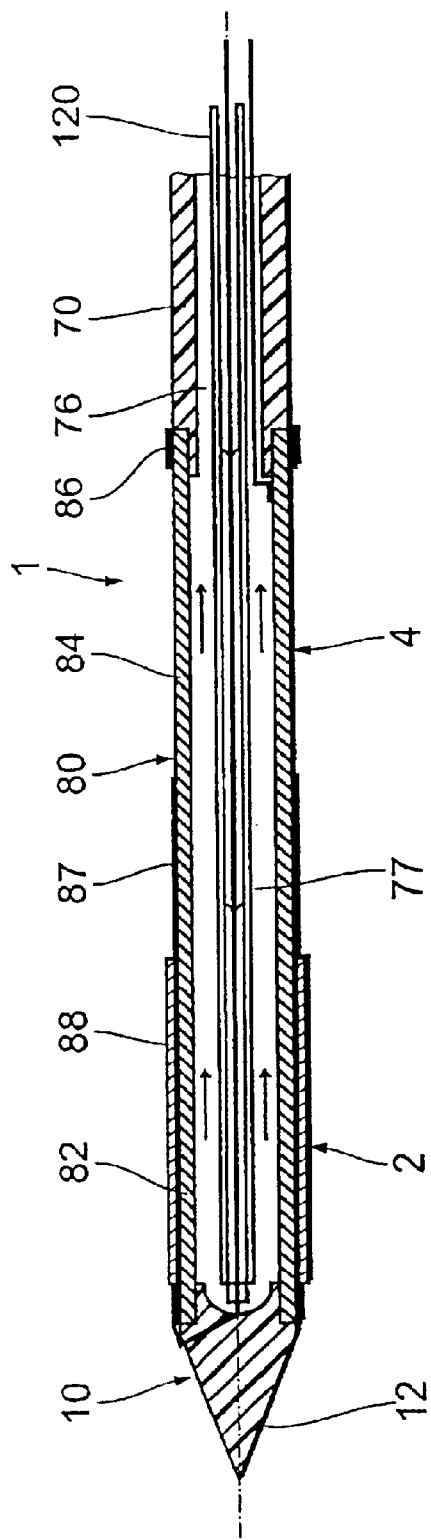

FIGS. 20 and 21 show further embodiments of a bipolar electrode arrangement. In both cases the basic structure provides a front cylinder 10 of metal or insulating material, adjoined by a tube 82 which is secured with the proximal end portion to a carrier 70. The carrier 70 and the tube 82 each have a respective central hollow duct 76 and 77 respectively through which is passed a flushing hoze or tube 110 which at its distal end discharges fluid which then in contact with the inside surface of the tube 82 flows back to the proximal end of the instrument. In FIG. 18 the distal tube portion 82 has a metallic outside surface and forms the cylindrical first electrode 2, the proximal tube portion 84 adjoining same is provided with an insulating layer 87 to which there is applied at the proximal end a metal layer 88 forming the cylindrical second electrode 4. In the embodiment of FIG. 19 in contrast the distal tube portion 82 is provided with an insulating layer 87 to which a metal layer 88 is applied at the distal end; the metal layer 88 forms the first electrode. In this embodiment the proximal tube portion forms the second electrode 4.

FIG. 24 shows a further embodiment of a bipolar electrode arrangement in which a carrier 70 comprising a metal tube extends to a wedge-shaped distal tip 12 and is in the shape of a cannula. An insulating layer 87 is applied to the carrier 70 at a predetermined spacing from the distal tip 12. In its proximal region the insulating layer 87 is provided with a metal coating 88. Adjoining the distal tip 12—with a metal outside surface—is the cylindrical first electrode 2 while the metal coating 88 at the proximal region forms the cylindrical second electrode 4. Extending through the tube is a hollow duct 76 which is open at the distal end and which can serve for introducing medication.

Figure 26:
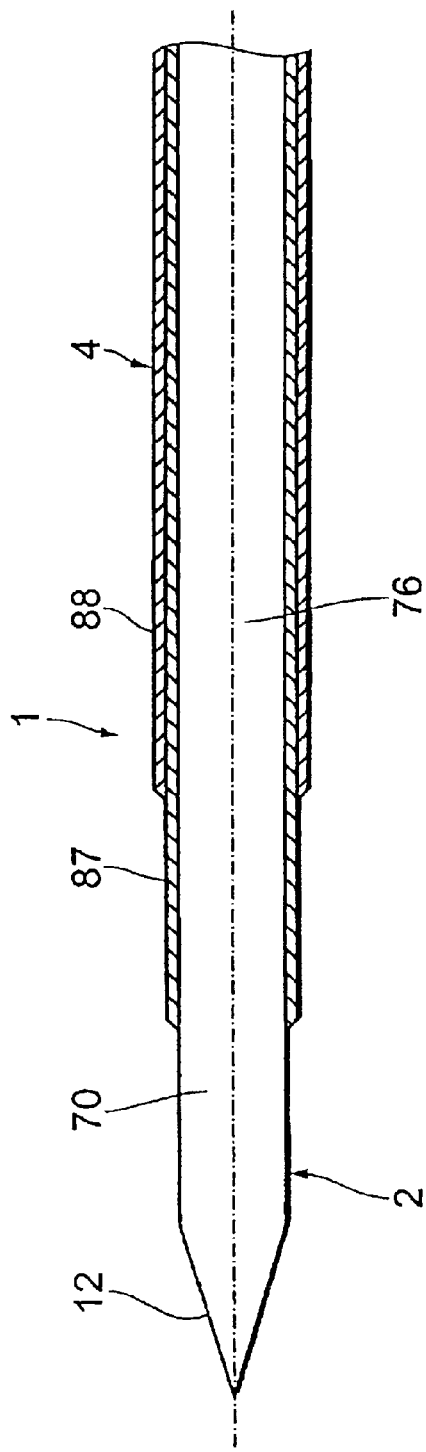

FIGS. 25 and 26 show alternative forms of the embodiment illustrated in FIG. 24. The embodiment of FIG. 25 differs from that shown in FIG. 24 insofar as the insulating layer 87 applied to the metal carrier 70 and the metal layer 88 applied to the insulating layer 87 each have a respective distal edge which corresponds to the wedge-shaped distal tip 12 of the carrier 70.

In the embodiment of FIG. 26, the carrier 70 is in the form of a metal bar (instead of the tubular carrier 70 in FIG. 24) which has a wedge-shaped distal tip and to which is applied the insulating layer 87 on which the metal layer 88 is then arranged.

All illustrated embodiments of the bipolar electrode arrangement 1 are essentially of a circular cross-section of a radius R and are of a cross-section which is as homogenous as possible over their length. Irregularities in outside diameter are to be minimised so that the electrode arrangement can be introduced into the tissue with an easy sliding movement.

In all illustrated embodiments the axial length of the electrodes is greater than the spacing of the electrodes which is substantially of the order of magnitude of the outside diameter. With this dimensioning, the arrangement affords advantageous local concentration of the coagulation procedure and adequate strength in terms of the electrical field involved. The carrier 70 can either be of a flexible or a rigid nature.

In all embodiments in which a flushing hoze or tube discharges flushing fluid at the distal end of a cavity, there is the option of providing for temperature control of the electrodes and the carrier before the electrode arrangement is introduced into the body, that is to say heating same to over 30° C. and preferably 50° C. In that way the electrode arrangement can be more easily introduced into the tissue. As soon then as the electrode arrangement has reached the treatment location and the actual electrothermal treatment is to be initiated, then to achieve an optimum coagulation procedure the instrument is cooled in order to prevent the tissue from drying out at the electrodes and in order to be able to apply higher levels of power and stronger electrical fields without the tissue becoming baked fast to the electrodes.

Figure 27:
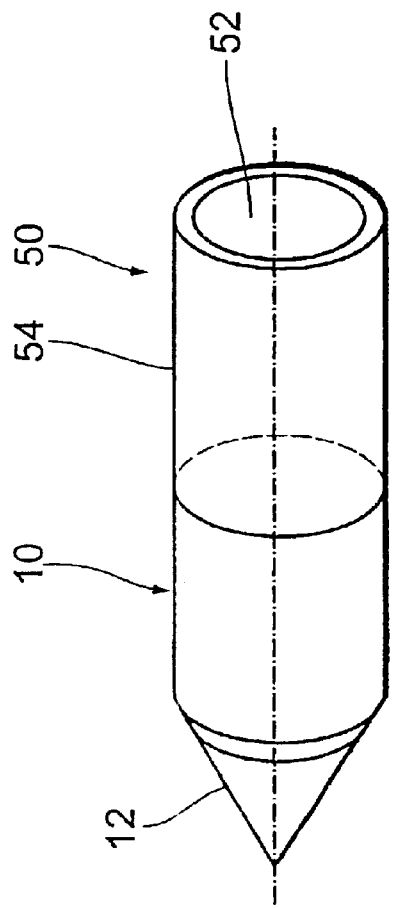

FIG. 27 shows a front cylinder 10 which comprises for example aluminum or titanium or a titanium alloy and which by anodic oxidation, that is to say in a proximal end region, was provided with a ceramic layer forming the insulating element 50 whose partition 52 is formed at the proximal end of the front cylinder and whose casing wall 58 extends on the outside around an axial lengthwise portion of the front cylinder.

FIGS. 28 and 29 show an end portion, in the form of a spiral spring 92, of a connecting line 90 which, as shown in FIG. 25, is inserted into the hollow duct 77 of a metal tube 80 and bears under radial contact pressure against the inside surface of the tube 80 and contacts same. An insulating layer 87 is illustrated on the metal tube 80.

FIGS. 30 and 31 show longitudinal section views of two embodiments of a bipolar electrode arrangement for a surgical instrument where the instrument extends angled in the longitudinal direction. Like parts have like reference numbers. FIGS. 30, 31 include lines 131, 131, respectively, indicating the instrument angled in the longitudinal direction.

What is claimed is:

1. A surgical instrument suitable for thermoelectric coagulation of tissue, the surgical instrument comprising:
   an electrically conductive front cylinder at a distal end of the instrument, the front cylinder having a distal tip and a cylindrical first electrode, wherein the first electrode includes an outside diameter;
   a tubular outer conductor proximate the front cylinder, the outer conductor having a cylindrical second electrode, wherein the second electrode includes an outside diameter, and wherein the first and second electrodes are adapted to be connected to a source of alternating voltage;
   an insulator element disposed between the front cylinder and the outer conductor;
   an inner conductor disposed within the outer conductor; and
   an insulating tube disposed between the inner conductor and the outer conductor;
   wherein the first electrode and the second electrode include substantially the same outside diameters.

2. The surgical instrument as set forth in claim 1 wherein the insulator has a radial partition between the front cylinder and the outer conductor, which at its outer edge goes into a cylindrical casing wall which surrounds the front cylinder and/or the outer conductor in snugly fitting relationship over a predetermined axial lengthwise portion, and that the inner conductor can be connected to the front cylinder through the partition of the insulator element.

3. The surgical instrument as set forth in claim 2 wherein the partition and the casing wall of the insulator element are applied in the form of a thin insulator layer to the front cylinder (10).

4. The surgical instrument as set forth in claim 1 characterized in that the front cylinder is of titanium or aluminum and the insulating element is surface-anodized in the form of a Ti or Al oxide layer on the front cylinder.

5. The surgical instrument as set forth in claim 2 wherein the insulating tube terminates distally with the outer conductor and bears against the partition of the insulator element.

6. The surgical instrument as set forth in claim 1 wherein the insulator is in the form of an annular body of a predetermined axial length having ends wherein the inner conductor extends through the annular body, and wherein the front cylinder and the outer conductor bear against the ends of the annular body.

7. The surgical instrument as set forth in claim 6 wherein the insulating annular body includes an at least partially translucent material.

8. The surgical instrument as set forth in claim 7 wherein the insulating annular body is a light source whose light issues in the form of scattered light through the insulating annular body.

9. The surgical instrument as set forth in claim 6 wherein the inner conductor has in the longitudinal direction a hollow duct which terminates in the insulating annular body and which accommodates an optical waveguide; wherein the region of the annular body the inner conductor has incisions extending radially into the fiber core of a optical waveguide, and forms a light source which discharges to the exterior through the insulating annular body of an at least partially translucent material the light which issues laterally from the optical waveguide in the form of scattered light.

10. The surgical instrument as set forth in claim 1 wherein the front cylinder is releasably connected to the inner conductor with a screw connection.

11. The surgical instrument as set forth in claim 10 wherein the inner conductor at its distal end carries a male screwthread that is adapted to be screwed to a corresponding female screwthread in the front cylinder.

12. The surgical instrument as set forth in claim 1 wherein the inner conductor, the outer conductor, the insulator element and the insulating tube comprise elastic material and are flexible.

13. The surgical instrument as set forth in claim 1 wherein the inner conductor and the outer conductor are rigid.

14. The surgical instrument as set forth in claim 1 wherein the outer conductor and the front cylinder extend straight over their axial length and are arranged in mutually coaxially aligned relationship.

15. The surgical instrument as set forth in claim 1 wherein the instrument extends angled in the longitudinal direction.

16. The surgical instrument as set forth in claim 1 wherein the outer conductor forms the second cylindrical electrode over the full lengthwise portion which is not covered by the insulator element.

17. The surgical instrument as set forth in claim 1 wherein the front cylinder forms the first electrode over its full lengthwise portion that is not covered by the insulator element.

18. The surgical instrument as set forth in claim 1 wherein the inner conductor and the front cylinder have a central hollow duct which issues from the distal tip of the front cylinder and includes an optical waveguide that is adapted to be supplied with laser signals.

19. The surgical instrument as set forth in claim 1 wherein the front cylinder and a proximate lengthwise portion comprises at least a partially translucent material and in a central opening contains a light source which discharges scattered light to the exterior.

20. The surgical instrument of claim 1 wherein the tip of the front cylinder terminates in a conical configuration.

21. The surgical instrument as set forth in claim 1 wherein the tip of the front cylinder terminates in a wedge-shaped configuration.

22. The surgical instrument as set forth in claim 1 wherein the axial length of the first and second electrodes is greater than the diameter of the electrodes.

23. The surgical instrument as set forth in claim 1 wherein the axial length of the first and second electrodes is greater than the axial length of the lengthwise portion occupied by the insulator element.

24. The surgical instrument as set forth in claim 1 wherein the axial length of the first and second electrodes is greater than the outside diameter of the front cylinder or the outer conductor respectively.

25. The surgical instrument as set forth in claim 1 wherein the axial spacing of the first and second electrodes from each other is approximately equal to or smaller than the outside diameter of the front cylinder.

26. The surgical instrument as set forth in claim 1 having connecting lines for connection of the first and second electrodes wherein at least one of the connecting lines includes at one end a portion of spring metal which is clamped radially outwardly in a hollow duct against an inside surface of the first and second electrodes.

* * * * *